(12) United States Patent
Hermansen et al.

(10) Patent No.: US 9,314,438 B2
(45) Date of Patent: Apr. 19, 2016

(54) ELEVATION OF THE PLASMA HDL-CHOLESTEROL LEVEL

(75) Inventors: Kjeld Hermansen, Egå (DK); Per Bendix Jeppesen, Egå (DK)

(73) Assignees: Aarhus Universitet, Aarhus C (DK); Region Midtjylland, Viborg (DK)

( * ) Notice: Subject to any disclaimer, the term of this patent is extended or adjusted under 35 U.S.C. 154(b) by 681 days.

(21) Appl. No.: 12/746,209

(22) PCT Filed: Dec. 5, 2008

(86) PCT No.: PCT/DK2008/050297
§ 371 (c)(1),
(2), (4) Date: Nov. 1, 2010

(87) PCT Pub. No.: WO2009/071099
PCT Pub. Date: Jun. 11, 2009

(65) Prior Publication Data
US 2011/0038827 A1      Feb. 17, 2011

(30) Foreign Application Priority Data
Dec. 5, 2007   (DK) .................................. 2007 01748

(51) Int. Cl.
*A61K 31/74*   (2006.01)
*A61K 31/19*   (2006.01)
*A61K 45/06*   (2006.01)

(52) U.S. Cl.
CPC .................. *A61K 31/19* (2013.01); *A61K 45/06* (2013.01)

(58) Field of Classification Search
CPC ............................. A61K 45/06; A61K 31/19
See application file for complete search history.

(56) References Cited

U.S. PATENT DOCUMENTS 6,140,342 A    10/2000  Goldstein et al.

FOREIGN PATENT DOCUMENTS

| CN | 101006995 | 8/2007 | |
| WO | 01/56959 | 8/2001 | |
| WO | 02/060419 | 8/2002 | |
| WO | 2006/116815 | * 11/2006 | ............. A61K 36/28 |
| WO | 2008/031439 | 3/2008 | |
| WO | 2008/134828 | 11/2008 | |

OTHER PUBLICATIONS

Of Gordon et al ("HighDensity Lipoprotein Cholesterol: and Cardiovascular Disease," Circulation 1989; 79:8-15).*
De Backer ("European guidelines to cardiovascular disease prevention in clinical practice," European Heart Journal, vol. 24, No. 17, pp. 1601-1610).*
Geuns et al ("Metabolism of stevioside in pigs and intestinal absorption characteristics of stevioside, rebaudioside A and steviol," Food and Chemical Toxicology 41 (2003) 1599-1607).*
Chan et al ("A Double-bind placebo-controlled study of the effectiveness and tolerability of oral stevioside in human hypertension," Br J Clin Pharmacol, 50, 215-220, 2000).*
Koyama et al ("In vitro metabolism of the glycosidic sweeteners, stevia mixture and enzymatically modified stevia in human intestinal microflora," Food and Chemical Toxicology 41 (2003) 359-374).*
Barriocanal et al ("Apparent lack of pharmacological effect of steviol glycosides used as sweeteners in humans. A pilot study of repeated exposures in some normotensiveand hypotensive individuals and in Type 1 and Type 2 diabetics," Regulatory Toxicology and Pharmacology 51 (2008) (37-41)).*
Savita et al ("Health Implications of Stevie rebaudiana," J. Hum. Ecol., 15(3): 191-194 (2004)).*
Avent et al. (1990); Hydrolysis of the diterpenoid glycoside, stevioside; Phytochemistry, vol. 29, No. 8, pp. 2712-2715.
Barter P. et al (2007); HDL Cholesterol, Very low levels of LDL Cholesterol, and cardiovascular events; N. Engl. J. Med., vol. 357, No. 13, pp. 1301-10.
Barter PJ et al., Illuminate Investigators (2007), Effects of torcetrapib in patients at high risk for coronary events; N. Engl. J. Med., vol. 357, No. 21, pp. 2109-22.
Blassetto JW et al. (2003); Efficacy of Rosuvastatin compared with other statins at selected starting doses in hypercholesterolemic patients and in special population groups; Am J Cardiol, vol. 91 (suppl), pp. 3C-10C.
Brown RJ. and Rader DJ. (2008); When HDL gets fat; Circulation Research, Journal of the American Heart Association, vol. 103, No. 2, pp. 131-2.
Castelli WP et al. (1986); Incidence of coronary heart disease and lipoprotein cholesterol levels: the Framingham Study; JMA, vol. 256, pp. 2835-2838.
Castle CK et al. (1998); Remodeling of the HDL in NIDDM: a fundemental role for cholesterol ester transfer protein; American Journal of Physiology, vol. 274, No. 6 pt.1, pp. E1091-98.
Davidson MH and Toth PP (2007); High-density lipoprotein metabolism: Potential therapeutic targets; The American Journal of Cardiology, vol. 100, No. 11A, pp. 32N-40N.
De Backer G et al. (2003); European guidelines on cardiovascular disease prevention in clinical practice. Third Joint Task Force of European and Other Societies on Cardiovascular Disease Prevention in Clinical Practice; European Heart Journal, vol. 24, No. 17, pp. 1601-1610.

(Continued)

*Primary Examiner* — Suzanne Ziska
(74) *Attorney, Agent, or Firm* — Posternak Blankstein & Lund LLP

(57) ABSTRACT

The present invention relates to the use of isosteviol, steviol, and related compounds for elevating the plasma HDL-cholesterol level. The invention furthermore relates to the use of these compounds for reducing the body weight of a subject and/or lowering the plasma triglyceride level of a subject, including a concomitant elevation of the plasma HDL-cholesterol level. Preferably the compounds used are isosteviol and/or steviol, or pharmaceutically acceptable salts, solvates or prodrugs thereof. The compounds may furthermore be administered in combination with one or more further active compounds, such as e.g. LDL-cholesterol lowering agents. The invention furthermore relates to a method for elevating the plasma HDL-cholesterol level in a subject by administering to a subject in need of such treatment a plasma HDL-cholesterol level elevating amount of the compounds, described herein.

31 Claims, 8 Drawing Sheets

(56) References Cited

OTHER PUBLICATIONS

Gordon et al. (1989); High-density lipoprotein and cardiovascular disease; Four prospective American studies. Circulation, vol. 79, pp. 8-15.

Green TJ. and Moghadasian MH. (2004); Species-related variations in lipoprotein metabolism: The impact of FER-HDL on susceptibility to atherogenesis; Life Sciences, vol. 74, pp. 2441-2449.

Heding LG (1972); Determination of total serum insulin (IRI) in insulin-treated diabetic patients; Diabetologica, vol. 8, pp. 260-266.

Hsu et al. (2002); in Microbial transformations of isosteviol; J. Nat. Prod., vol. 65, pp. 273-277.

Jeppesen PB et al. (2006); Can Stevioside in combination with soy-based dietary supplement be a new useful treatment in type 2 diabetetes? An in vivo study in the diabetic goto-kakizaki rat; Rev Diabetic Stud, vol. 3, pp. 189-199.

Johnson R et al. (1997); Use of the friedewald formula to estimate LDL-cholesterol in patients with chronic renal failure on dialysis; Clinical Chemistry, vol. 43, pp. 2183-2184.

Kohda H et al. (1976); New diterpene glucosides from Stevia rebaudiana; Phytochemistry, vol. 15, pp. 981-983.

Mann JI et al. (2004); Diabetes and Nutrition Study Group (DNSG) of the European Association. Evidence-based nutritional approaches to the treatment and prevention of diabetes mellitus; Nutr. Metab. Cardiovasc. Dis., vol. 14, No. 6, pp. 373-94.

Melnikova I (2005); Raising HDL cholesterol; Nature Reviews, vol. 4, pp. 185-186.

Mosca L et al. and American Heart Association (2004); Evidence-based guidelines for cardiovascular disease prevention in women; Circulation, vol. 109, No. 5, pp. 672-693.

Nordentoft I et al. (2008); Isosteviol increases insulin sensitivity and changes gene expression of key insulin regulatory genes and transcription factors in islets of the diabetic KKAy mouse; Diabetes Obes Metab, vol. 10, No. 10, pp. 939-49.

Ogawa T et al. (1980); Total synthesis of stevioside; Tetrahedron, vol. 36, No. 18, pp. 2641-2648.

Rader DJ (2007); Illuminating HDL—Is it still a viable therapeutic target?; N. Engl. J. Med.; vol. 357, No. 21, pp. 2180-2183.

Singh IM et al. (2007); High-density lipoprotein as a Therapeutic target: A systematic review; JAMA, vol. 298, No. 7, pp. 786-798.

Smith SC et al. (2006); AHA/ACC guidelines for secondary prevention for patients with coronary and other atherosclerotic vascular disease: 2006 update: endorsed by the National Heart, Lung, and Blood Institute; Circulation, vol. 113, No. 19, pp. 2363-2372.

Stampfer M et al. (1991); A prospective study of cholesterol, apolipoproteins, and the risk of myocardial infarction; N. Engl J Med, vol. 325, pp. 373-381.

Wong et al. 2006. "Antiproliferative effect of isosteviol on angiotensin-II-treated rat aortic smooth muscle cells". Pharmacology, 76:163-169.

Wong K et al. (2004); Isosteviol acts on potassium shannels to relax isolated aortic strips of wistar rat; Life Science, vol. 74, pp. 2379-2387.

Wong KL et al. (2004); Isosteviol as a potassium channel opener to lower intracellular calcium concentrations in cultured aortic smooth muscle cells; Planta Med, vol. 70, pp. 108-112.

Xu D et al. (2007); The cardioprotective effect of isosteviol on rats with hear ischemia-reperfusion injury; Life Science, vol. 80, pp. 269-274.

Xu D et al. (2007); The effects isosteviol against myocardium injury induced by ischaemia-reperfusion in the isolated gunea pig heart; Clinical and experimental pharmacology, vol. 34, pp. 488-493.

\* cited by examiner

A

B

ELEVATION OF THE PLASMA HDL-CHOLESTEROL LEVEL

FIELD OF INVENTION

The present invention relates to the use of isosteviol, steviol, and related compounds for elevating the plasma HDL-cholesterol level, lowering the plasma triglyceride level and/or reducing the body weight of a subject.

BACKGROUND OF INVENTION

Risk for development of diseases and conditions like atherosclerosis, coronary artery disease, and coronary heart disease have been shown to be strongly correlated with certain plasma lipid levels. While elevated levels of low density lipoprotein-cholesterol (LDL-cholesterol) may be the most recognized form of dyslipidemia, it is by no means the only significant lipid associated contributor to e.g. coronary heart disease. Low levels of high density lipoprotein-cholesterol (HDL-cholesterol) is also a known risk factor for coronary heart disease (Gordon, D. J., et al., "High-density Lipoprotein Cholesterol and Cardiovascular Disease", Circulation, (1989), 79: 8-15).

The risk for developing e.g. cardiovascular diseases is positively correlated with high levels of LDL-cholesterol and triglycerides, while high levels of HDL-cholesterol are negatively correlated. More specifically, in the range from 0.5 mmol/l to 3 mmol/l an increase in the HDL-cholesterol level minimizes the risk for developing e.g. cardiovascular diseases.

Thus, dyslipidemia is not a unitary risk profile for diseases like coronary heart disease but may be comprised of one or more lipid aberrations.

Atherosclerosis and its associated coronary artery disease is the leading cause of mortality in the industrialized world. Despite attempts to modify secondary risk factors (smoking, obesity, lack of exercise) and treatment of dyslipidemia with dietary modification and drug therapy, coronary heart disease remains the most common cause of death in the U.S., where cardiovascular disease accounts for 44% of all deaths, with 53% of these associated with atherosclerotic coronary heart disease.

It has recently been investigated to what extent high and low levels of LDL- and HDL-cholesterol are indicative for the occurrence of major cardiovascular events. The study evaluated the effect of HDL-cholesterol levels in patients with clinically evident coronary heart disease who received statin therapy to reduce LDL-cholesterol levels. It was found that HDL cholesterol levels were predictive of major cardiovascular events in patients treated with statins, however, this relationship was also observed among patients with LDL-cholesterol levels below 70 mg/dL (see Philip Barter et al: "*HDL Cholesterol, Very low levels of LDL Cholesterol, and Cardiovascular events*"; N. Engl. J. Med., 2007, 357, (13), 1301-10). Although statin treatment provides an overall improvement in outcomes, clinical trial data reveal a significant number of cardiac events despite reaching targeted LDL levels. Accordingly, to reduce the risk of cardiovascular events it is not enough merely to lower the level of LDL-cholesterol but is can also be recommended to increase the level of HDL-cholesterol.

For instance a HDL-cholesterol level of less than 35 mg/dl (1.0 mmol/l) for men and less than 42 mg/dl (1.20 mmol/l) for women is a maker for an increased risk of e.g. cardiovascular diseases (see: *Prevention of cardiovascular diseases in clinical practice*. Guidelines of the third joint task force of European and other societies on cardiovascular disease prevention in clinical practice. European Heart Journal 2003; 24:1601-1610).

The American Heart Association recommends a plasma HDL-cholesterol level for adult men and women with an increased risk of cardiovascular diseases of above 40 mg/dl (1.18 mmol/l) and above 50 mg/dl (1.29 mmol/l), respectively. (L. Mosca, L. J. Appel, E. J. Benjamin et al. and American Heart Association, *Evidence-based guidelines for cardiovascular disease prevention in women*, Circulation; 109 (2004) (5), 672-693).

An analysis of data from four large studies has also previously been published, showing that each increase of 1 mg/dl (0.03 mmol/l) in HDL-cholesterol is associated with a decrease of 2 to 3% in the risk of future coronary heart disease. (Gordon et al. *High-density lipoprotein and cardiovascular disease*. Four prospective American studies. Circulation 1989; 79:8-15.)

Recently, a phase 3 clinical trial with a cholesteryl ester transfer protein (CETP) inhibitor, torcetrapib, was terminated because of increased mortality in the active treatment group (see Barter, P J, et al.; ILLUMINATE Investigators, *Effects of torcetrapib in patients at high risk for coronary events*, N Engl J Med 2007, 22; 357(21):2109-22). Accordingly, the previously believed theory that CETP inhibition could raise the HDL-cholesterol level suffered a blow. (See Rader, D. J.; *Illuminating HDL—Is it still a viable therapeutic target?*; N. Engl. J. Med.; 2007; 357; 21, p. 2180-2183).

No wholly satisfactory HDL-elevating therapies exist. Statins that are now widely used to lower LDL cholesterol levels in people with—or at risk of acquiring—cardiovascular disease, lower cholesterol by inhibiting the enzyme HMG-CoA reductase. Hereby is obtained an increased clearance of LDL from the bloodstream and a decrease in the blood cholesterol level. However, the administration of statins can be associated with safety issues such as e.g. serious but uncommon musculoskeletal reactions like rhabdomyolysis. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well-tolerated agent which can significantly elevate plasma HDL levels, thereby reversing or slowing the progression of diseases like atherosclerosis.

SUMMARY OF INVENTION

The present invention relates to compounds with the core structure of formula (I), or pharmaceutically acceptable salts, solvates or prodrugs thereof, for elevating the plasma HDL-cholesterol level. The compounds of the present invention can be used to elevate the plasma HDL-cholesterol level in various forms of lipid aberrations. In one form of a lipid aberration the fasting total plasma cholesterol level is in a normal range, but the plasma HDL-cholesterol level may still be relatively low compared to the normal distribution between HDL-, LDL- and VLDL-cholesterol. In another form of a lipid aberration the fasting total plasma cholesterol level is elevated compared to the normal range, whereas the plasma HDL-cholesterol level is relatively low compared to the normal distribution between HDL-, LDL- and VLDL-cholesterol. In both forms such an imbalance will give an increased risk of developing diseases or conditions—and/or exacerbating an existing disease or condition—as for example atherosclerosis and cardiovascular diseases. The invention furthermore relates to a lowering of the plasma triglyceride level in addition to an elevation of the plasma HDL-cholesterol level, the triglyceride level may be measured as either the fasting or the non-fasting plasma triglyceride level. In a preferred embodiment the compound is selected from the group consisting of isosteviol and steviol, or pharmaceutically acceptable salts, solvates or prodrugs thereof, for elevating the plasma HDL-cholesterol level to a level of at least 35 mg/dl (1.0 mmol/l) for men and a level of at least 42 mg/dl (1.20 mmol/l) for women; more preferably the compound is isosteviol, or pharmaceutically acceptable salts, solvates or prodrugs thereof.

The present invention furthermore relates to the compounds with the core structure of formula (I), or pharmaceutically acceptable salts, solvates or prodrugs thereof, for reducing the body weight of a subject, such as e.g. for the treatment of adiposity, and/or for elevating the plasma HDL-cholesterol level.

DETAILED DESCRIPTION OF THE INVENTION

Figure 1:
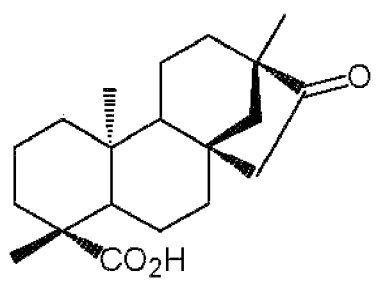
FIGS. 1A and 1B shows the structure of isosteviol and steviol, respectively
Figure 1:
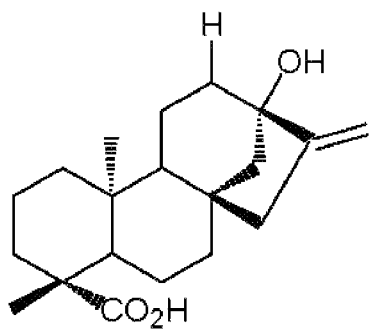

The present inventors have surprisingly found that compounds with the core structure of formula (I) can be used to elevate the plasma HDL-cholesterol level.

Accordingly, the present invention relates to a compound with the core structure of formula (I)

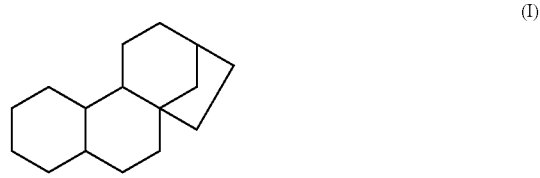 [SMILES: C1CCC2C(C1)CCC13CCC(CCC21)C3]

(I)

wherein the core structure is substituted with one or more substituents at any chemically feasible positions, or pharmaceutically acceptable salts, solvates or prodrugs thereof, for elevating the plasma HDL-cholesterol level.

In a preferred embodiment of the invention the core structure of formula (I), is a core structure of formula (II)

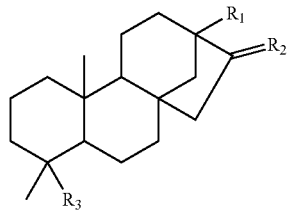

(II)

wherein
R$_1$ is selected from the group consisting of —C$_{1-6}$alkyl, —O—C$_{1-6}$alkyl, —OH, and —OC(O)(C$_{1-6}$alkyl), —COO (C$_{1-6}$alkyl);
R$_2$ is selected from the group consisting of CH$_2$, O, and CH(C$_{1-6}$alkyl);
R$_3$ is selected from the group consisting of —COOH, —COO (C$_{1-6}$alkyl), —C(O)NH(C$_{1-6}$alkyl), —C(O)-(common amino acid moiety); and
wherein the core structure optionally is further substituted with one or more substituents at any chemically feasible positions.

The inventors have surprisingly found that the compounds of the present invention can be used to elevate the plasma HDL-cholesterol level in various forms of lipid aberrations. For instance, when the fasting total plasma cholesterol level is in a normal range, the plasma HDL-cholesterol level may still be relatively low compared to the normal distribution between HDL-, LDL- and VLDL-cholesterol, hereby giving an increased risk of developing diseases or conditions described herein—and/or exacerbating an existing disease or condition—as for example atherosclerosis and cardiovascular diseases.

In another form of lipid aberration the fasting total plasma cholesterol level is elevated compared to the normal range, whereas the plasma HDL-cholesterol level is relatively low compared to the normal distribution between HDL-, LDL- and VLDL-cholesterol. As in the above-mentioned case, such an imbalance will give an increased risk of developing diseases or conditions described herein—and/or exacerbating an existing disease or condition—as for example atherosclerosis and cardiovascular diseases.

The compounds of the present invention can in both cases specifically elevate the plasma HDL-cholesterol level whereby the plasma lipid balance is restored; hereby eliminating the increased risk for developing a disease or condition and/or treating an existing disease or condition that otherwise would be exacerbated.

Hence, the compounds according to the present invention due to their specifically plasma HDL-cholesterol elevating effect are useful for the treatment and correction of the various dyslipidemias observed to be associated with the development and incidence of atherosclerosis, peripheral vascular disease, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, or vascular complications of diabetes.

In one embodiment of the invention the compounds of the invention are administered to healthy subjects having a high risk profile for developing a diseases or condition as above mentioned. Subjects having a high risk profile are traditionally identified by for example a family history with premature cardiovascular disease or by other risk factors such as smoking and hypertension. However, in the future said subjects may also be identified by for example a specific gene profile showing the increased risk. Accordingly, by identifying subjects with a high risk profile and treating low levels of HDL-cholesterol with a compound according to the present invention the risk of developing the above mentioned diseases, such as e.g., a cardiovascular disease, is significantly decreased.

In one specific embodiment of the invention the subject is a subject not suffering from diabetes mellitus or Type 2 diabetes. In a further specific embodiment of the invention the subject is a healthy subject without diabetes mellitus or Type 2 diabetes.

The term "C$_{1-6}$alkyl" means a saturated linear or branched hydrocarbon group including, for example, methyl, ethyl, isopropyl, t-butyl, pentyl, hexyl, and the like.

The term "common amino acid moiety" means the naturally occurring α-amino acids, unnatural amino acids, substituted β and γ amino acids and their enantiomers. Non-limiting examples are alanine, β-alanine, arginine, asparagine, aspartic acid, cysteine, glutamic acid, glutamine, glycine, histidine, isoleucine, leucine, lysine, methionine, phenylalanine, praline, serine, threonine, tryptophan, tyrosine, valine, 3-hydroxyproline, N-methylphenylalanine, N-methylisoleucine, norvaline, norleucine, ornithine, 2-aminobutyric acid, 2-aminoadipic acid, methionine sulfoxide, methionine sulfone, phenylglycine, o-methyltyrosine, etc.

As is well understood in this technical area, a large degree of substitution is not only tolerated, but is often advisable. Substitution is anticipated on the core structure of compounds to be used in the present invention. The term "substituents" are used to differentiate between the core structure of formula (I) and formula (II) and further chemical species that may be substituted on to the core structure. Non-limiting examples of suitable substituents may be hydrocarbon alkyl substituents, such as methyl, ethyl, propyl, t-butyl, and the like, and further substituents known in the art, such as hydroxy, alkoxy, alkylsulfonyl, halogen, cyano, nitro, amino, carboxyl, aryl, heteroaryl, cycloalkyl, common amino acids etc. It is well-known that these substituents may include further substitution, such for example, alkyl, aryl, heteroaryl etc. bearing further substituents known in the art, such as hydroxy, alkoxy, alkylsulfonyl, halogen atoms, cyano, nitro, amino, carboxyl, common amino acids etc.

The term "aryl" means a mono- or polycyclic aromatic hydrocarbon group.

The term "heteroaryl" means a monovalent aromatic cyclic radical having one to three rings, of four to eight atoms per ring, incorporating one or two heteroatoms (chosen from nitrogen, oxygen, or sulphur) within the ring.

The term "cycloalkyl" means a monovalent saturated carbocyclic radical consisting of one, two or three rings, of three to eight carbons per ring.

When the compounds of the present invention contain asymmetric carbon atoms, the pharmaceutical acceptable salts, solvates and prodrugs may exist as single stereoisomers, racemates, and/or mixtures of enantiomers and/or diastereomers. All such single stereoisomers, racemates, and mixtures thereof are intended to be within the scope of the present invention.

An even more preferred embodiment of the present invention relates to a compound selected from the group consisting of isosteviol and steviol, or pharmaceutically acceptable salts, solvates or prodrugs thereof, for elevating the plasma HDL-cholesterol level. In a preferred embodiment, the compound is isosteviol, or pharmaceutically acceptable salts, solvates or prodrugs thereof. Alternatively, the compound is steviol, or pharmaceutically acceptable salts, solvates or prodrugs thereof. However, in some embodiments the compound may furthermore be a mixture of steviol and isosteviol, or pharmaceutically acceptable salts, solvates or prodrugs thereof. The structure of isosteviol (ent-16-ketobeyeran-19-oic acid) and steviol (ent-kaur-16-en-13-ol-19-oic acid) can be seen in FIGS. 1A and 1B, respectively.

A preferred embodiment of the invention relates to the compounds for elevating the plasma HDL-cholesterol level in an animal, and more preferably a human subject.

It is normally considered that subjects having a plasma HDL-cholesterol level of less than 35 mg/dl (1.0 mmol/l) for men and less than 42 mg/dl (1.20 mmol/l) for women are having an increased risk of e.g. cardiovascular diseases. Accordingly, in one embodiment of the present invention, the plasma HDL-cholesterol level is elevated to a level of at least 35 mg/dl (1.0 mmol/l) for men and a level of at least 42 mg/dl (1.20 mmol/l) for women. However, in another embodiment of the present invention relating to subjects having a high risk profile the plasma HDL-level is elevated to at least 40 mg/dl (1.18 mmol/l) for men and at least 50 mg/dl (1.29 mmol/l) for women. Accordingly, the plasma HDL-cholesterol level is preferably elevated to at least 42 mg/dl, more preferably elevated to at least 50 mg/dl, and even more preferably elevated to at least 55 mg/dl.

It is furthermore recognized that for each increase of 1 mg/dl (0.03 mmol/l) in the plasma HDL-cholesterol level the relative risk of acquiring a future cardiovascular heart disease is decreased by 2 to 3%. Accordingly, each increase in the plasma HDL-cholesterol level, being small or large, is of relevance for decreasing the risk of acquiring low HDL-cholesterol associated diseases and conditions as discussed herein above. Therefore in a preferred embodiment of the invention, the plasma HDL-cholesterol level is elevated by at least 2 mg/dl (0.06 mmol/l), such as more preferably by at least 3 mg/dl (0.09 mmol/l). Another way of expressing the increase in HDL-cholesterol provided by the present invention is therefore in relative terms, i.e. in percentage of the starting value for the specific subject in question. In one embodiment of the invention the HDL-cholesterol level is elevated by about 5% to about 50%, preferably from about 5% to about 40%, more preferably from about 10% to about 40%, and even more preferably from about 10% to about 30%.

The term "fasting" is in the present invention defined as lack of food intake for at least 10 hours—normally from 10 p.m. to 8 a.m.—in which period water intake is allowed.

Besides low levels of plasma HDL-cholesterol a further indicator of an increased risk of acquiring diseases and conditions as above described is the fasting plasma triglyceride level. Subjects having a fasting plasma triglyceride concentration of more than 1.7 mmol/l are considered to have an increased risk. Accordingly, in one embodiment of the present invention, the compounds according to the invention are used to elevate the plasma HDL-cholesterol level and at the same time lower the fasting plasma triglyceride level. Preferably, the fasting plasma triglyceride level is lowered to a concentration below 1.7 mmol/l, more preferably to a concentration below 1.5 mmol/l and even more preferably to a concentration below 1.2 mmol/l.

However, as there may be variations between subjects with regard to which concentration of plasma triglycerides is relevant, another way of expressing the decrease is therefore in relative terms, i.e. in percentage of the starting value for the specific subject in question. In one embodiment of the invention the plasma triglycerides level is lowered by about 5% to about 50%, preferably from about 10% to about 50%, more preferably from about 20% to about 50%, and even more preferably from about 20% to about 40%. This way of expressing a decrease is furthermore relevant when the plasma triglyceride level is not measured as a fasting plasma triglyceride level, but instead as a non-fasting level. It is to be understood that the compounds of formula (I) decreases the plasma triglyceride level, irrespective of whether it is measured as a fasting or a non-fasting plasma triglyceride level. Accordingly, in one embodiment of the present invention, the compounds according to the invention are used to elevate the plasma HDL-cholesterol level and at the same time lower the plasma triglyceride level.

It has recently been found that the plasma triglyceride level can be determined as a non-fasting level, and that this non-fasting plasma triglyceride level has an even better correlation to the risk of obtaining a cardiovascular disease, than the fasting plasma triglyceride level. Accordingly, in one embodiment of the present invention, the compounds according to the invention are used to elevate the plasma HDL-cholesterol level and at the same time lower the plasma triglyceride level. The lowering of the plasma triglyceride level may for this purpose be expressed in relative terms, i.e. as a percentage of the starting value for the specific subject in question. Accordingly, in one embodiment of the invention the plasma triglycerides level is lowered by about 5% to about 50%, preferably from about 10% to about 50%, more preferably from about 20% to about 50%, and even more preferably from about 20% to about 40%.

The inventors of the present invention have found that the plasma triglyceride level of a subject is significantly reduced upon treatment with isosteviol, when said subject is on a normal diet, see the examples herein. Preferably the subject is a mammal, and more preferably the subject is a human. Accordingly, a preferred embodiment of the present invention relates to compounds of the invention, such as preferably isosteviol and/or steviol, more preferably isosteviol, or pharmaceutically acceptable salts, solvates or prodrugs thereof, for lowering the plasma triglyceride level of a subject being on a normal diet, and optionally at the same time elevating the HDL plasma cholesterol level, as described herein.

Furthermore, a specific embodiment of the present invention relates to compounds of the invention, such as preferably isosteviol and/or steviol, more preferably isosteviol, or pharmaceutically acceptable salts, solvates or prodrugs thereof, for lowering the plasma triglyceride level of a subject being on a normal diet, and optionally at the same time elevating the HDL plasma cholesterol level; where said subject is not suffering from diabetes mellitus or Type 2 diabetes. For this embodiment the further features mentioned herein apply mutatis mutantis.

Furthermore, the compounds of the invention according to formula (I) may be used for reducing the body weight of a subject; preferably a subject being classified as obese, and for example a subject being obese and having an increased risk of acquiring diseases and conditions as described herein. Accordingly, in one embodiment of the present invention, the compounds according to the invention are for at the same time elevating the plasma HDL-cholesterol level and reducing the body weight of a subject. As the reduction in body weight will be dependent on the starting weight of the subject, the reduction may be expressed in relative terms, i.e. in percentage of the starting value for the specific subject in question. Preferably the body weight is reduced by at least about 5%, preferably at least about 8%, more preferably at least about 10%, even more preferably at least about 12%, yet even more preferably at least about 15%, such as e.g. at least about 18%, at least about 20%, at least about 22%, or at least about 25%.

A further aspect of the present invention relates to a compound with the core structure of formula (I)

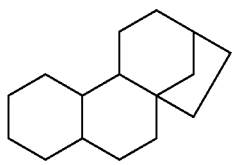

(I)

wherein the core structure is substituted with one or more substituents at any chemically feasible positions, or pharmaceutically acceptable salts, solvates or prodrugs thereof, for reducing the body weight of a subject.

Preferred embodiment and further features of this aspect of the present invention relating to reducing the body weight of a subject, are described herein above and below for the aspect of the invention relating to elevation of the HDL plasma cholesterol level, and apply mutatis mutandis for this aspect relating to reducing the body weight. This applies for instance for details as to the compounds of formula (I), the daily dosage administered, a possible combination treatment where a further active substance is administered, and/or the formulation of the compounds of formula (I) as described in the section "formulation".

It is especially preferred to use a compound selected from the group consisting of isosteviol and steviol, or pharmaceutically acceptable salts, solvates or prodrugs thereof, for reducing the body weight of a subject. Even more preferably the compound is isosteviol, or pharmaceutically acceptable salts, solvates or prodrugs thereof. Alternatively, the compound is steviol, or pharmaceutically acceptable salts, solvates or prodrugs thereof. However, in some embodiments the compound may furthermore be a mixture of steviol and isosteviol, or pharmaceutically acceptable salts, solvates or prodrugs thereof. Preferably the invention relates to the compounds for reducing the body weight in an animal subject, and more preferably a human subject.

The body weight is preferably reduced by at least about 5%, preferably at least about 8%, more preferably at least about 10%, even more preferably at least about 12%, yet even more preferably at least about 15%, such as e.g. at least about 18%, at least about 20%, at least about 22%, or at least about 25%.

In a specific embodiment of this aspect of the invention the reduction in body weight is dependent on the diet. Preferably, the subject being treated is on a diet selected from the group consisting of a normal diet, an energy reduced diet, a low fat diet, a low carbohydrate diet, a high fiber diet, and a protein rich diet. More preferably, the subject being treated is on a diet selected from the group consisting of a normal diet, an energy reduced diet and a low fat diet. Preferably the body weight is reduced by at least about 5%, preferably at least about 8%, more preferably at least about 10%, even more preferably at least about 12%, yet even more preferably at least about 15%, such as e.g. at least about 18%, at least about 20%, at least about 22%, or at least about 25%. This may for example be the case when the subject being treated is on a normal diet, such as e.g. a non-high fat diet.

As used herein the term "normal diet" is intended to mean a diet having a balanced energy distribution between carbohydrates, fat and protein, i.e. not for example a diet having a high fat content or a diet having a high carbohydrate content. For mammals a normal diet will be dependent on the specific type of mammal. For humans a "normal diet" may be defined as a diet having the following energy distribution: 45-60% from carbohydrates, <35% from fat and 10-20% from protein (see e.g. Mann, J. I. et al., *Diabetes and Nutrition Study Group (DNSG) of the European Association. Evidence-based nutritional approaches to the treatment and prevention of diabetes mellitus*, Nutr Metab Cardiovasc Dis., 2004, 14(6):373-94). For rodents such as e.g. mice and rats, a "normal diet" may be exemplified by a chow diet, which have the following distribution: 71% carbohydrates, 5% lipids, and 24% protein, (see e.g. Nordentoft, I. et al., *Isosteviol increases insulin sensitivity and changes gene expression of key insulin regulatory genes and transcription factors in islets of the diabetic KKAy mouse*, Diabetes Obes Metab., 2008, 10(10):939-49).

Furthermore the term an "energy reduced diet", as used herein, including, but not limited to, a "low fat diet", is intended to mean a diet where <30% of the energy originates from fat. The term "low carbohydrate diet", as used herein, is intended to mean a diet where <40% of the energy originates from carbohydrates. The terms "high fiber diet" or "protein rich diet", as used herein, is intended to mean a diet where >20% of the energy originates from protein (for definitions see e.g. Mann, J. I. et al., *Diabetes and Nutrition Study Group (DNSG) of the European Association. Evidence-based nutritional approaches to the treatment and prevention of diabetes mellitus*, Nutr Metab Cardiovasc Dis., 2004, 14(6):373-94).

In a further embodiment of this aspect of the invention the compounds are for at the same time reducing the body weight of a subject and elevating the plasma HDL-cholesterol level. The plasma HDL-cholesterol level is preferably elevated as defined above under the first aspect of the invention.

The inventors of the present invention have found that the body weight is significantly reduced upon treatment with isosteviol, when said subject is on a normal diet, see the examples herein. Preferably the subject is a mammal, and more preferably the subject is a human. Accordingly, a preferred embodiment of this aspect of the invention relates to compounds of the invention, such as preferably isosteviol and/or steviol, more preferably isosteviol, or pharmaceutically acceptable salts, solvates or prodrugs thereof, for reducing the body weight of a subject being on a normal diet, and optionally at the same time elevating the HDL plasma cholesterol level, as described herein.

Furthermore, a specific embodiment of this aspect of the invention relates to compounds of the invention, such as preferably isosteviol and/or steviol, more preferably isosteviol, or pharmaceutically acceptable salts, solvates or prodrugs thereof, for reducing the body weight of a subject being on a normal diet, and optionally at the same time elevating the HDL plasma cholesterol level; where said subject is not suffering from diabetes mellitus or Type 2 diabetes. For this embodiment the further features mentioned herein apply mutatis mutandis.

In another further embodiment of this aspect of the invention the compounds are for at the same time reducing the body weight of a subject and lowering the fasting plasma triglyceride level. The fasting plasma triglyceride level is preferably lowered as defined above under the first aspect of the invention, such as for example by about 5% to about 50%, and the subject is for example on a normal diet.

In a preferred embodiment of this aspect of the invention the compounds are for at the same time reducing the body weight of a subject, elevating the plasma HDL-cholesterol level, and lowering the plasma triglyceride level. The reduction in body weight, the elevation of the plasma HDL-cholesterol and the lowering of the plasma triglyceride level is preferably as defined above for the first aspect of the invention.

The term "pharmaceutically acceptable" means that the compound or composition must be compatible with the other ingredients of a formulation, and not deleterious to the patient.

The terms "treating", "treat" or "treatment" include both preventative (e.g., prophylactic), palliative, and curative treatment, together with a treatment to reduce symptoms.

As used herein, the term "salt" includes, but is not limited to, any possible base or acid addition salts of the compounds of the present invention. The acid addition salts are formed from basic compounds, whereas the base addition salts are formed from acidic compounds. All of these forms are within the scope of the present invention. A non-toxic pharmaceutically acceptable base addition salt of an acidic compound may be prepared by contacting the free acid form of the compound with a sufficient amount of a desired base to produce the salt in the conventional manner. The free acid form of the compound may be regenerated by contacting the salt form so formed with an acid, and isolating the free acid of the compound in the conventional manner. The free acid forms of the compounds differ from their respective salt forms somewhat in certain physical properties such as solubility, crystal structure, hygroscopicity, and the like, but otherwise the salts are equivalent to their respective free acid for purposes of the present invention. Non limiting examples of counter ions for the base additions salts are a metal cation, such as an alkali or alkaline earth metal cation, or an amine, especially an organic amine. Examples of suitable metal cations include sodium cation (Na+), potassium cation (K+), magnesium cation (Mg2+), calcium cation (Ca2+), and the like. Examples of suitable amines are N,N'-dibenzylethylenediamine, chlorprocaine, choline, diethanolamine, dicyclohexylamine, ethylenediamine, N-methylglucamine, and procaine (see, for example, Berge S. M. et al., "Pharmaceutical Salts," J. of Pharma. Sci., 1977; 66:1).

As used herein, the term "solvate" means a compound of the invention or a salt thereof that further includes a stoichiometric or non-stoichiometric amount of a solvent bound by non-covalent intermolecular forces. Preferred solvents are volatile, non-toxic, and/or acceptable for administration to humans in trace amounts. The solvated forms, including hydrated forms, are equivalent to unsolvated forms and are encompassed within the scope of the present invention.

As used herein, the term "prodrug" means a compound that is transformed in vivo to yield a compound of the present invention. The transformation may occur by various mechanisms, such as through hydrolysis in blood. For example, when a compound of the present invention contains a carboxylic acid functional group, a prodrug can comprise an ester formed by the replacement of the hydrogen atom of the acid group with a group including, but not limited to, groups such as for example $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N (alkoxycarbonyl)amino)ethyl having from 4 to 10 carbon atoms, 3-phthalidyl, 4 crotonolactonyl, gamma-butyrolacton-4-yl, di-N,N—$(C_1-C_2)$alkylamino$(C_2-C_3)$alkyl, carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl. The a prodrug can furthermore comprise e.g. an amide formed by the replacement of the hydrogen atom of an acid group with a common amino acid moiety, non-limiting examples of common amino acids are mentioned herein above.

Different species have different distributions between the HDL-, LDL- and VLDL-cholesterol in the total plasma cholesterol. For example in rodents as e.g. in mice and rats, the major part of the total plasma cholesterol is formed by HDL-cholesterol. This is in contrast to human subjects where LDL-cholesterol constitutes the main component of total plasma cholesterol and HDL-cholesterol normally only forms a small part. Elevated total plasma cholesterol in mice thus can reflect a high HDL-cholesterol and a beneficial lipid profile, whereas a high total cholesterol level in humans normally is caused by elevated LDL cholesterol, i.e. a negative lipid profile.

In the context of the present invention, the term "daily dosage" is meant to describe the daily dosage required for an average human subject having a weight of about 70 kg. In general, for administration to human patients the daily dosage level of the compounds in accordance with the present invention, is in a range of from about 10 mg to about 1500 mg.

In one embodiment of the invention the compound is given in a daily dosage in a range of from about 10 mg to about 500 mg, such as e.g., from about 20 mg to about 500 mg, about 30 mg to about 500 mg, about 40 mg to about 500 mg, about 50 mg to about 500 mg, about 100 mg to about 500 mg, about 10 mg to about 400 mg, about 10 mg to about 300 mg, about 10 mg to about 200 mg, about 10 mg to about 100 mg, about 100 mg to about 500 mg, about 100 mg to about 400 mg, about 100 mg to about 300 mg, about 100 mg to about 200 mg, about 200 mg to about 500 mg, about 200 mg to about 400 mg, or about 200 mg to about 300 mg.

In another embodiment of the invention the compound is given in a daily dosage in a range of from about 500 mg to about 1000 mg, such as e.g., from about 500 mg to about 900 mg, about 500 mg to about 800 mg, about 500 mg to about 700 mg, about 500 mg to about 600 mg, about 600 mg to about 1000 mg, about 700 mg to about 1000 mg, about 800 mg to about 1000 mg, about 900 mg to about 1000 mg, or about 600 mg to about 900 mg.

In yet another embodiment of the invention the compound is given in a daily dosage in a range of from about 1000 mg to about 1500 mg, such as e.g., from about 1000 mg to about 1400 mg, about 1000 mg to about 1300 mg, about 1000 mg to about 1200 mg, about 1000 mg to about 1100 mg, about 1100 mg to about 1500 mg, about 1200 mg to about 1500 mg, about 1300 mg to about 1500 mg, about 1400 mg to about 1500 mg, or about 1100 mg to about 1400 mg.

In a preferred embodiment of the invention the compound is isosteviol and the daily dosage is in a range of from about 100 mg to about 1000 mg, preferably from about 500 mg to about 1000 mg.

The skilled person will readily be able to determine the dosage levels required for a subject whose weight falls outside the average range, such as children and the elderly. The daily dosage may optionally be administered as a single dose or be divided in two or more doses, such as e.g. two, three, or four, for administration at different times during the day. The skilled person will appreciate that, in the treatment of insulin resistance or diseases associated with insulin resistance, compound used in accordance with the presents invention may be taken as a single dose on an "as required" basis, i.e., as needed. The physician will in any event determine the actual dosage which will be most suitable for any particular patient and it will vary with the age, weight and response of the particular patient. The above dosages are, of course only exemplary of the average case and there may be instances where higher or lower doses are merited and such are within the scope of the invention.

Another way of expressing the daily dosage level in accordance with the present invention is as mg/kg. Accordingly, for administration to human patients the daily dosage levels of the compounds in accordance with the present invention, or pharmaceutically acceptable salts, solvates or prodrugs thereof, will be in a range from about 0.14 to about 21 mg/kg, preferably from about 1.5 to about 14 mg/kg, and more preferably from about 7 to about 14 mg/kg.

In one embodiment of the present invention, the compounds are formulated in a composition for oral, peroral, sublingual, parenteral, intramuscular, topical, buccal, nasal, or inhalation administration. In a preferred embodiment of the present invention, the composition is for oral administration.

In a further embodiment of the invention, the compound is isolated from a plant source. For this purpose may be used the leaves of *Stevie rebaudiana Bertoni*, or other members of the Stevia family.

Combination Therapy

The compounds in accordance with the present invention may be administered alone, or as part of a combination therapy. If a combination of active agents is administered, then it may be administered simultaneously, separately or sequentially. Depending on the disease and the state of the disease to be treated, it may be relevant to include one or more additional active compound in the composition. Accordingly, in one embodiment of the invention, the compound is formulated in a composition further comprising one or more additional active compounds. However in another embodiment the compounds of the invention are administered in combination with one or more additional active compounds. The one or more additional active compound may preferably be selected from the group consisting of LDL-cholesterol lowering agents, triglyceride lowering agents, cholesterol synthesis inhibitors, cholesterol absorption inhibitors, MTP/Apo B secretion inhibitors, and other cholesterol lowering agents such as fibrates, niacin, ion-exchange resins, antioxidants, ACAT inhibitors and bile acid sequestrants. In combination therapy treatment, both the compounds of this invention and the other active compounds may be administered to mammals (e.g., humans, male or female) by conventional methods.

In one embodiment of the present invention, the compounds for elevating plasma HDL-cholesterol levels are administered in combination with one or more additional active compounds selected from the group consisting of insulin, sulfonylureas, meglitinides, biguanides, thiazolidinediones, glitazones, α-glucosidase inhibitors, incretin mimetics such as e.g. GLP-1 analogues and GLP-1 agonists, DPP-4 inhibitors, amylin analogues, PPAR α/γ ligands, sodium-dependent glucose transporter 1 inhibitors, fructose 1,6-bisphosphatase inhibitors, glucagon inhibitors, and 11beta-HSD1 inhibitors. Non-limiting examples of the one or more additional active compound may be selected from the group consisting of insulin, glimepiride, glibenclamide, tolbutamide, gliclazide, glipzid, repaglinide, nateglinide, metformin, pioglitazones, rosiglitazones, acarbose, miglitol, liraglutide, exenatide, sitagliptin, vildagliptin, saxagliptin, and alogliptin.

In another embodiment of the present invention, the compounds for elevating plasma HDL-cholesterol levels are administered in combination with one or more additional active compounds selected from the group consisting of insulin, sulfonylureas, meglitinides, biguanides, thiazolidinediones, glitazones, α-glucosidase inhibitors, incretin mimetics such as e.g. GLP-1 analogues and GLP-1 agonists, DPP-4 inhibitors, amylin analogues, PPAR α/γ ligands, sodium-dependent glucose transporter 1 inhibitors, fructose 1,6-bisphosphatase inhibitors, glucagon inhibitors, glucagon blockers, glucokinase stimulating agents, and 11beta-HSD1 inhibitors.

In another embodiment of the present invention the one or more additional active compounds are selected from the group consisting of thiazides, diuretics, ACE inhibitors, AT2 inhibitors, ARB, $Ca^{2+}$ antagonists, α-blockers, β-blockers, cholesterol absorption inhibitors, hypolipidemic drugs, fibrates, anion exchangers, bile acid sequestrants, fish oils, HMG-CoA reductase inhibitors, and CB1 cannabinoid receptor antagonists. Non-limiting examples of the one or more additional active compound may be selected from the group consisting of bendroflumetiazid, indapamid, hydrochlorothiazid, captopril, enalapril, lisinopril, fosinopril, perindopril, quinapril, ramipril, trandolapril, quinapril, fosinopril, candesartancilexetil, irbesartan, losartan, valsartan, telmisartan, eprosartan, olmesartanmedoxomil, nifedipin, amlodipin, nitrendipin, diltiazem, felodipin, verapamil, lacidipin, isradipin, lercanidipin, doxazosin, prazosin, terazosin, phentolamin, hydralazin, acebutolol, atenolol, bisoprolol, carvedilol, esmolol, labetalol, metoprolol, pindolol, propranolo, sotalol, tertatolol, timolol, methyldopa, moxonidin, ezitimibe, gemfibrozil, bezafibrat, fenofibrate, nicotinic acid, acipimox, colestipol, colestyramin, fish oils, atorvastatin, fluvastatin, lovastatin, pravastatin, rosuvastatin, simvastatin, rosuvastatin, pitavastatin, mevastatin, cerivastatin, and rimonabant.

In another embodiment of the present invention the one or more additional active compounds are selected from the group consisting of thiazides, diuretics, ACE inhibitors, AT2 inhibitors, ARB, $Ca^{2+}$ antagonists, α-blockers, β-blockers, cholesterol absorption inhibitors, hypolipidemic drugs, fibrates, anion exchangers, bile acid sequestrants, fish oils, HMG-CoA reductase inhibitors, CB1 cannabinoid receptor antagonists, and aldosteron blocking agents.

In a preferred embodiment of the invention the one or more additional active compounds is a LDL-cholesterol lowering agents. In a more preferred embodiment the one or more LDL-cholesterol lowering agents is selected from the group consisting of HMG-CoA reductase inhibitors and MTP/Apo B inhibitors. Non-limiting examples of HMG-CoA reductase inhibitors that may be used are atorvastatin, fluvastatin, lovastatin, pravastatin, rosuvastatin, simvastatin, rosuvastatin, pitavastatin, mevastatin, and cerivastatin. The term HMG-COA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455-509 and references cited therein). A variety of these compounds are described and referenced above however other HMG-CoA reductase inhibitors will be known to those skilled in the art. U.S. Pat. No. 4,231,938 discloses certain compounds isolated after cultivation of a microorganism belonging to the genus *Aspergillus*, such as lovastatin. Also, U.S. Pat. No. 4,444,784 discloses synthetic derivatives of the aforementioned compounds, such as simvastatin. Also, U.S. Pat. No. 4,739,073 discloses certain substituted indoles, such as fluvastatin. Also, U.S. Pat. No. 4,346,227 discloses ML-236B derivatives, such as pravastatin. Also, EP-491226A discloses certain pyridyldihydroxyheptenoic acids, such as rivastatin. In addition, U.S. Pat. No. 5,273,995 discloses certain 6-[2-(substituted-pyrrol-1-yl)alkyl]pyran-2-ones such as atorvastatin.

In an even more preferred embodiment of the invention the compound according to the invention is administered in combination with one or more additional active compounds selected from the group consisting of LDL-cholesterol lowering agents, triglyceride lowering agents, cholesterol synthesis inhibitors, cholesterol absorption inhibitors, MTP/Apo B secretion inhibitors, and other cholesterol lowering agents such as fibrates, niacin, ion-exchange resins, antioxidants, ACAT inhibitors and bile acid sequestrants for at the same time elevating the plasma HDL-cholesterol level and lowering the LDL-cholesterol level. Non-limiting examples of LDL-cholesterol lowering agents are HMG-CoA reductase inhibitors, such as statins, and MTP/Apo B secretion inhibitors. This embodiment would for instance be relevant in a situation as described herein above, where the fasting total plasma cholesterol level is elevated compared to the normal range, whereas the plasma HDL-cholesterol level is relatively low compared to the normal distribution between HDL-, LDL- and VLDL-cholesterol. Such an imbalance will give an increased risk of developing diseases or conditions described herein—and/or exacerbating an existing disease or condition—as for example atherosclerosis and cardiovascular diseases. The LDL-cholesterol level is preferably lowered to less than 3 mmol/l. For subjects having an increased risk of developing cardiovascular diseases the LDL-cholesterol level is preferably lowered to less than 2.5 mmol/l, such as e.g. to less than 2.0, and more preferably to less than 1.8 mmol/l.

In another preferred embodiment of the invention the compound according to the invention is administered in combination with one or more additional active compounds selected from the group consisting of LDL-cholesterol lowering agents, triglyceride lowering agents, cholesterol synthesis inhibitors, cholesterol absorption inhibitors, MTP/Apo B secretion inhibitors, and other cholesterol lowering agents such as fibrates, niacin, ion-exchange resins, antioxidants, ACAT inhibitors and bile acid sequestrants for at the same time elevating the plasma HDL-cholesterol level and lowering the fasting total plasma cholesterol level. The fasting total plasma cholesterol level is preferably lowered to less than 5 mmol/l. For subjects having an increased risk of developing cardiovascular diseases the fasting total plasma cholesterol level is preferably lowered to less than 4.5 mmol/l.

In a specific embodiment of the invention the one or more additional active compounds, such as for example LDL-cholesterol lowering agents, triglyceride lowering agents, cholesterol synthesis inhibitors, cholesterol absorption inhibitors, MTP/Apo B secretion inhibitors, and other cholesterol lowering agents, is not selected from the group consisting of soy protein, soybean fibres, such as e.g. cotyledon fibres, and phytoestrogens, and mixtures thereof. Accordingly, in this embodiment of the invention the soy protein, soybean fibres and phytoestrogens are neither present alone or in mixtures in a composition according to the invention, nor are they administered in combination with a composition according to the invention.

In another specific embodiment of the invention the one or more additional active compounds are not selected from bile salts, bile salt derivatives or mixtures thereof. Examples of bile salt derivatives include, but are not limited to, synthetic bile salts, modified bile acids as described in U.S. Pat. No. 5,641,767, nor- and homo-bile acid derivatives as described in U.S. Pat. No. 5,656,277, bile acid derivatives as described in U.S. Pat. Nos. 5,610,151 and 5,428,182, esters and salts of bile acids as described in U.S. Pat. No. 3,910,888, all of which hereby are incorporated by reference. Accordingly, in this embodiment of the invention bile salts, bile salt derivatives or mixtures thereof are neither present alone or in mixtures in a composition according to the invention, nor are they administered in combination with a composition according to the invention.

The above-mentioned plasma levels of HDL-cholesterol, LDL-cholesterol, fasting plasma triglycerides, non-fasting plasma triglycerides, and fasting total plasma cholesterol may be measured by any standard method applied in the field. Non-limiting examples are for instance where the fasting plasma triglyceride level is measured by the enzymatic colorimetric GPO-PAP method (Glycerol phosphate oxidase±phenol 4 amino phenazon), based on Trinder, using commercially available test kits (Roche Diagnostics, Basel, Germany), and the Cobas Mira instrument (Roche Diagnostics); and the fasting total plasma cholesterol level and the HDL-cholesterol level are measured by an enzymatic colorimetric test, the "cholesterol CHOD-PAP" method (cholesterol oxidase±phenol 4 amino phenazon), based on Trinder, using commercially available test kits (Roche Diagnostics, Basel, Germany), and the Cobas Mira instrument (Roche Diagnostics). The HDL plasma cholesterol level may be determined as a fasting or as a non-fasting level. The plasma LDL-cholesterol level can be measured directly, or may—when the triglyceride concentration is less than 4.5—be estimated by use of the Friedewald formula (concentrations in mmol/l):

LDL-cholesterol=total cholesterol−HDL-cholesterol−(0.456×total triglycerides)

In another preferred embodiment of the invention the one or more additional active compounds is any MTP/Apo B secretion (microsomal triglyceride transfer protein and or apolipoprotein B) inhibitor. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R. 1992; Science 258:999). A variety of these compounds are described and referenced herein, however other MTP/Apo B secretion inhibitors will be known to those skilled in the art. WO 96/40640 and WO 98/23593 are two exemplary publications relating to such compounds. For example, the following MTP/Apo B secretion inhibitors are particularly useful:

4'-trifluoromethyl-biphenyl-2-carboxylic acid[2-(1H-[1,2,4,]triazol-3-ylmethyl)-1,2,3,4-tetrahydro-isoquinolin-6-yl]-amide;

4'-trifluoromethyl-biphenyl-2-carboxylic acid[2-(2-acetylamino-ethyl)-1,2,3,4-tetrahydro-isoquinolin-6-yl]-amide;

(2-{6-[(4'-trifluoromethyl-biphenyl-2-carbonyl)-amino]-3,4-dihydro-1H-isoquinolin-2-yl)}ethyl)-carbamic acid methyl ester;

4'-trifluoromethyl-biphenyl-2-carboxylic acid[2-(1H-imidazol-2-ylmethyl)-1,2,3,4-tetrahydro-isoquinolin-6-yl]-amide;

4'-trifluoromethyl-biphenyl-2-carboxylic acid[2-(2,2-diphenyl-ethyl)-1,2,3,4-tetrahydro-isoquinolin-6-yl]-amide; and 4'-trifluoromethyl-biphenyl-2-carboxylic acid[2-(2-ethoxy-ethyl)-1,2,3,4-tetrahydro-isoquinolin-6-yl]-amide.

Method of Treatment

The present invention furthermore encompasses a method for elevating the plasma HDL-cholesterol level in a subject by administering to a subject in need of such treatment a plasma HDL-cholesterol level elevating amount of a compound with the core structure of formula (I), as defined above. In preferred embodiments of the method according to the invention, the core structure of formula (I), is a core structure of formula (II), as defined above. In a more preferred embodiment of the method according to the invention the compound is selected from the group consisting of steviol or isosteviol, or pharmaceutically acceptable salts, solvates or prodrugs thereof. In an even more preferred embodiment of the method according to the invention the compound is isosteviol, or pharmaceutically acceptable salts, solvates or prodrugs thereof.

In a further embodiment of the method for elevating the plasma HDL-cholesterol level in a subject, the compounds according to the invention are used to elevate the plasma HDL-cholesterol level and at the same time lower the plasma triglyceride level. The lowering of the plasma triglyceride level may for this purpose be expressed in relative terms, see herein above for further features relating to the plasma triglyceride level.

In one embodiment of the invention the subject is a mammal, such as a human. In a more preferred embodiment the subject is a human and the daily dosage is in a range of from about 10 mg to about 1500 mg. Further preferred embodiments of the daily dosage are described herein above.

The present invention furthermore encompasses a method for reducing the body weight of a subject by administering to a subject in need of such treatment a body weight reducing amount of a compound with the core structure of formula (I), as defined above. In preferred embodiments of the method according to the invention, the core structure of formula (I), is a core structure of formula (II), as defined above. In a more preferred embodiment of the method according to the invention the compound is selected from the group consisting of steviol or isosteviol, or pharmaceutically acceptable salts, solvates or prodrugs thereof. In an even more preferred embodiment of the method according to the invention the compound is isosteviol, or pharmaceutically acceptable salts, solvates or prodrugs thereof. In a specific embodiment of this method the subject being treated is on a diet selected from the group consisting of a normal diet, an energy reduced diet, a low fat diet, a low carbohydrate diet, a high fiber diet, and a protein rich diet. More preferably, the subject being treated is on a diet selected from the group consisting of a normal diet, an energy reduced diet and a low fat diet.

Preferably the body weight is reduced by at least about 5%, preferably at least about 8%, more preferably at least about 10%, even more preferably at least about 12%, yet even more preferably at least about 15%, such as e.g. at least about 18%, at least about 20%, at least about 22%, or at least about 25%. This may for example be the case when the subject being treated is on a normal diet, such as e.g. a non-high fat diet.

As described herein above, the body weight is significantly reduced upon treatment with isosteviol, when said subject is on a normal diet, see the examples herein. Accordingly, a preferred embodiment of the method relates to compounds of the invention, preferably isosteviol or steviol, more preferably isosteviol, or pharmaceutical acceptable salts, solvents or prodrugs thereof, for reducing the body weight of a subject being on a normal diet, and optionally at the same time elevating the HDL plasma cholesterol level, as described herein. A further specific embodiment of the method for reducing the body weight of a subject relates to compounds of the invention, such as preferably isosteviol and/or steviol, more preferably isosteviol, or pharmaceutically acceptable salts, solvates or prodrugs thereof, for reducing the body weight of a subject being on a normal diet, and optionally at the same time elevating the HDL plasma cholesterol level; where said subject is not suffering from diabetes mellitus or Type 2 diabetes.

The subject in need of treatment in the methods according to the present invention may be healthy subject having a high risk profile for developing a diseases or conditions as for example atherosclerosis, peripheral vascular disease, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, or hypertension. In one specific embodiment of the methods according to the invention the subject is a subject not suffering from diabetes mellitus or Type 2 diabetes. In a further embodiment of the methods according to the invention the subject is a healthy subject without diabetes mellitus or Type 2 diabetes.

The features mentioned above for a compound, or pharmaceutically acceptable salt, solvates or prodrugs thereof, for elevating the plasma HDL-cholesterol level, and/or reducing body weight, and/or lowering the plasma triglyceride level apply mutatis mutandis for the methods of treatment according to the present invention.

Formulations

For use in the present invention the compounds may be administered alone, but will generally be administered in admixture with suitable pharmaceutical excipients, diluents or carriers selected with regard to the intended route of administration and standard pharmaceutical practice. Accordingly, in one embodiment of the invention the compounds according to the invention are formulated in a composition optionally with one or more pharmaceutical excipients, diluents or carriers.

In a specific embodiment of the invention a compound with the core structure of formula (I) or formula (II), is in a composition as the only active compound, in admixture with suitable pharmaceutical excipients, diluents or carriers. Accordingly, said composition may be a pharmaceutical composition consisting of one or more compounds with the core structure of formula (I) or formula (II), preferable one or more compounds selected from the group consisting of isosteviol and steviol, or pharmaceutically acceptable salts, solvates or prodrugs thereof, more preferably isosteviol, for elevating the plasma HDL-cholesterol level and/or reducing the body weight of a subject.

More specifically in one embodiment of the invention a pharmaceutical composition does not comprise one or more compounds selected from the group consisting of soy protein, soybean fibres, such as e.g. cotyledon fibres, phytoestrogens, bile salts, and bile salt derivatives. Even more specifically said pharmaceutical composition does not comprise one or more compounds selected from the group consisting of soy protein, soybean fibres, such as e.g. cotyledon fibres, and phytoestrogens. Alternatively, said pharmaceutical composition does not comprise one or more bile salts or bile salt derivatives.

In a specific embodiment of the invention the compound or one or more compounds of formula (I) is the only active compounds administered for elevating the plasma HDL-cholesterol level and/or for reducing the body weight of a subject. The compound of formula (I) in it self, i.e. for example and preferably steviol and/or isosteviol, is capable of providing the elevation in the plasma HDL-cholesterol level and/or the reduction in the body weight.

For example, the compounds to be used in accordance with the invention can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via fast dispersing or fast dissolving dosage forms. The compounds of the invention are preferably administered orally, such as e.g. by a pharmaceutical composition formulated for oral administration.

Tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatine and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating. Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug compound used i.e. where the drug compound is insoluble a fast dispersing dosage form can be prepared and where the drug compound is soluble a fast dissolving dosage form can be prepared.

In general a tablet formulation could typically contain between about 10 mg to about 1500 mg of a compound for use in accordance with the present invention (or a salt, solvate or prodrug thereof) whilst tablet fill weights may for example range from 50 mg to 3000 mg. An example formulation for a tablet is illustrated here:

| Ingredient | % w/w |
|---|---|
| Steviol, Isosteviol, or salts, solvates or prodrugs thereof | 10.000* |
| Lactose | 64.125 |
| Starch | 21.375 |
| Croscarmellose Sodium | 3.000 |
| Magnesium Stearate | 1.500 |

*This quantity is typically adjusted in accordance with the desired dosage.

Another example formulation is illustrated here:

| Ingredient | Amount, mg |
|---|---|
| Isosteviol | 100* |
| Starch | 259 |
| Lactose | 259 |
| Magnesium stearate | 3.3 |
| Talc | 29.7 |

*This quantity is typically adjusted in accordance with the desired dosage

The above example formulations may further contain e.g. colour, flavour or a coating in order to disguise an unpleasant taste.

As mentioned above, the daily dosage of the compounds of the invention, including steviol and isosteviol, or pharmaceutically acceptable salts, solvates or prodrugs thereof will be from about 0.14 to about 21 mg/kg (in single or divided doses), preferably in a range from about 1.5 to about 14 mg/kg, and more preferably from about 7 to about 14 mg/kg. Thus, tablets or capsules will for example contain 10 mg to 1.5 g of compound for administration singly or two or more at a time, as appropriate.

For aqueous suspensions and/or elixirs, the compounds of the invention, or the pharmaceutically acceptable salts, solvates or prodrugs thereof, may be combined with various sweetening or flavouring agents, colouring matter or dyes, with emulsifying and/or suspending agents and with diluents such as water, ethanol, propylene glycol and glycerin, and combinations thereof.

The compounds for use in accordance with the invention can also be administered parenterally, for example, intravenously, intra-arterially, intraperitoneally, intrathecally, intraventricularly, intraurethrally, intramuscularly or subcutaneously, or they may be administered by infusion techniques. For such parenteral administration medicaments are best used in the form of a sterile aqueous solution which may contain other compounds, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The compounds for use in accordance with the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetra-fluoro-ethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of compound for use in accordance with the invention and a suitable powder base such as lactose or starch. The compounds for use in accordance with the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds for use in accordance with the invention can be administered by the rectal or topical route. This may be in the form of a suppository, or by topical application in the form of a gel, hydrogel, lotion, solution, cream, ointment, dusting powder or skin patch. For application topically to the skin, the compounds can be formulated as a suitable ointment containing the active compound suspended or dissolved in, for example, a mixture with one or more of the following: mineral oil, liquid petrolatum, white petrolatum, propylene glycol, polyoxyethylene, polyoxypropylene compound, emulsifying wax and water. Alternatively, the compounds can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyldodecanol, benzyl alcohol and water.

The compounds for use in accordance with of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

In addition to the above described formulations, medicaments containing a compound for use in accordance with the present invention may furthermore be prepared by conventional techniques, e.g. as described in Remington: The Science and Practice of Pharmacy 1995, edited by E. W. Martin, Mack Publishing Company, 19th edition, Easton, Pa.

Preparation of Active Compounds of the Invention

The active compounds of formula (I) herein may be obtained by any known procedures. For example steviol and isosteviol may be prepared from stevioside by the procedures described by Ogawa, T. et al., *Total Synthesis of Stevioside*, Tetrahedron, (1980), 36(18), 2641-2648; or Anthony G. Avent et al., *hydrolysis of the diterpenoid glycoside, stevioside*, Phytochemistry, 1990, vol. 29, No. 8, pp. 2712-2715, which preparation procedures hereby are incorporated by reference. Stevioside may for example be obtained from *Stevie rebaudiana*. The preparation of isosteviol from stevioside by acid hydrolysis and subsequent purification by recrystallization has furthermore been reported by Feng-Lin Hsu et al, in *Microbial transformations of isosteviol*, J. Nat. Prod. (2002), 65, 273-277, wherein there is also reported the microbial preparation of further compounds of formula (I); all of which preparations hereby are incorporated by reference.

EXAMPLES

Example 1

Figure 2:
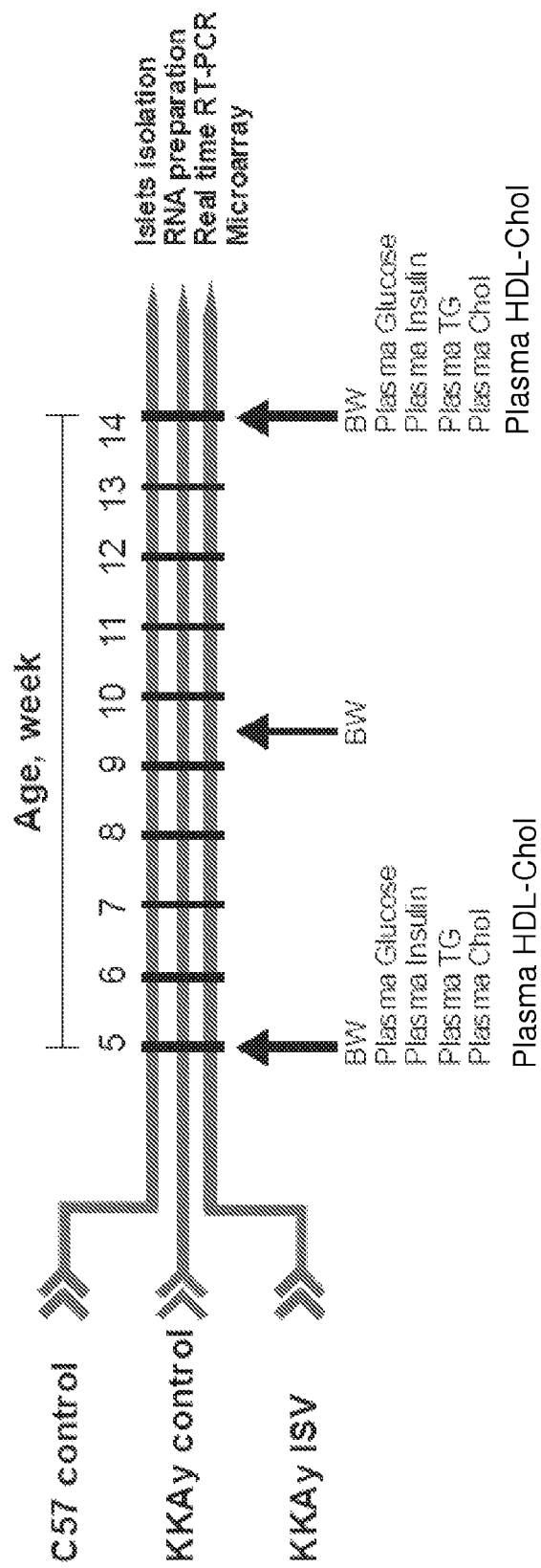
FIG. 2 shows the study design of the in vivo study described in example 1.

In Vivo Study: the Effects of Isosteviol Treatment on the Plasma HDL-Cholesterol Level Materials and Methods:
Animals Twenty male KKAy-mice (Clea Japan, Tokyo, Japan), all 5 week-old, weighing 22-25 g were randomized to 2 groups and treated for 9 weeks with; A: standard chow diet (control); B: standard chow diet+20 mg/kg BW of ISV. As a non-diabetic control group (C), ten normal C57BL-mice (Taconic, Ry, Denmark) were fed with standard chow diet (control to A), see FIG. 2 for outline of the study. The food intake was measured halfway through the study. The composition of the standard chow diet dry matter was: Protein 24%, carbohydrate 71%, and Lipids 5%. The drug isosteviol (ISV, ent-16-ketobeyeran-19-oic acid; Wako Pure Chemical Industries, Osaka, Japan) was incorporated in the mice food pellet and administered orally. The Danish Council for Animal experiments has approved the study.

Plasma Analysis

Hormones and lipids were measured from blood sample at start and end of the treatment period. Blood sample was taken from the tail of the animals on chilled tubes containing heparin/aprotinin and centrifuged (4000 g, 60 seconds, 4° C.), and plasma was frozen for subsequent analysis of insulin, glucose, triglycerides, total cholesterol and HDL-cholesterol. Fasting blood glucose, as well as bodyweight (BW), was measured before and after intervention.

Assays

Plasma blood glucose was determined using the glucose oxidase method (GOD-PAP, Boehringer Mannheim, GmbH Germany). Insulin was determined by radioimmunoassay with a guinea pig antiporcine insulin antibody (PNILGP4, Novo Nordisk, Bagsvaerd, Denmark), and mono-[$^{125}$I]-(TyrA14) labeled human insulin (Novo Nordisk) as tracer and rat insulin (Novo Nordisk) as standard. We separated free and bound radioactivity using ethanol (See Heding L. G. *Determination of total serum insulin (IRI) in insulin-treated diabetic patients*; Diabetologia 1972; 8:260-266). Interassay and intra-assay variation was below 10%. ISV did not interfere with the insulin assay at the concentrations studied. The fasting plasma triglyceride level was measured by the enzymatic colorimetric GPO-PAP method (Glycerol phosphate oxidase±phenol 4 amino phenazon), based on Trinder, using commercially available test kits (Roche Diagnostics, Basel, Germany), and the Cobas Mira instrument (Roche Diagnostics). The fasting total plasma cholesterol level and the HDL-cholesterol level were measured by an enzymatic colorimetric test, the "cholesterol CHOD-PAP" method (cholesterol oxidase±phenol 4 amino phenazon), based on Trinder, using commercially available test kits (Roche Diagnostics, Basel, Germany), and the Cobas Mira instrument (Roche Diagnostics).

Statistical Analysis

Data are expressed as means±standard error of the mean (SEM). Statistical significance between two groups was evaluated using a two-tailed t test. A p value of less than 0.05 was considered statistically significant. For plasma glucose calculations, analysis of covariance with adjustment for end body weight was performed.

Results:

Changes in Fasting Total Plasma Cholesterol Level

Figure 3:
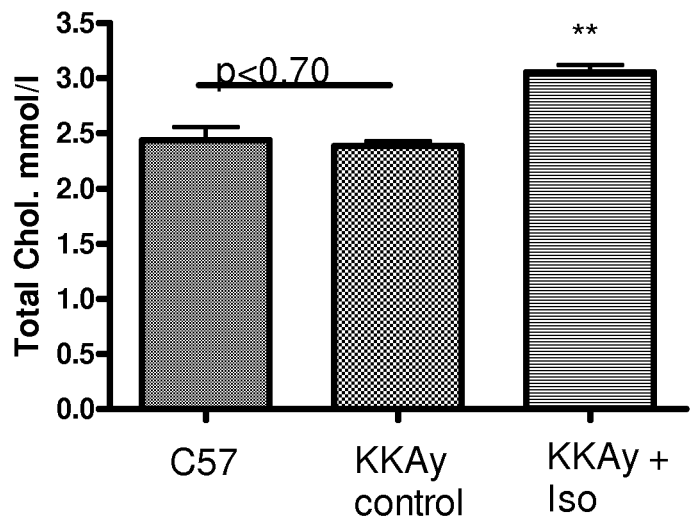
FIG. 3 shows the effect of isosteviol treatment on fasting plasma total-cholesterol in KKAy mice after 9-weeks interventions. The animals were 5 weeks of age when the treatment began. The C57BL and KKAy control groups received standard chow diet and the isosteviol (ISV) group received standard chow supplemented with 20 mg isosteviol/kg body weight/day. Data are shown as mean±SEM (n=10 in each group). (unpaired), ** p<0.0001.

The effect of ISV treatment on the fasting plasma total cholesterol level in the KKAy group after 9-weeks interventions can be seen from FIG. 3. The fasting total plasma cholesterol level has increased by 28%. Data are shown in FIG. 3 as mean±SEM (n=10 in each group). (unpaired), ** p<0.0001. Mean±SEM: C57: 2.436±0.122; KKAy: 2.385±0.046; KKAy+Iso: 3.055±0.067.

In rodents as e.g. in mice and rats, the major part of total cholesterol is formed by HDL-cholesterol. This is in contrast to human subjects where LDL-cholesterol constitutes the main component of total cholesterol and HDL cholesterol only forms a small part. Elevated total cholesterol in mice thus reflects a high HDL cholesterol and a beneficial lipid profile, whereas a high total cholesterol in humans normally is caused by elevated LDL cholesterol, i.e. a negative lipid profile.

Changes in Plasma HDL-Cholesterol Level

Figure 4:
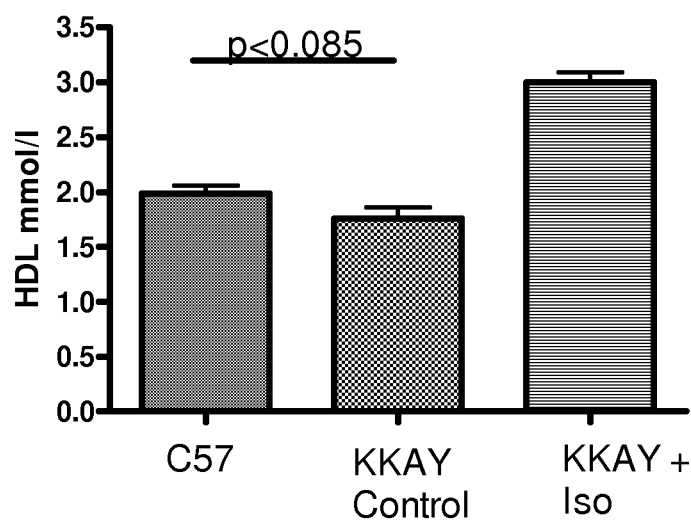
FIG. 4 shows the effect of isosteviol treatment on fasting plasma HDL-cholesterol in KKAy mice after 9-weeks interventions. The animals were 5 weeks of age when the treatment began. The C57BL and KKAy control groups received standard chow diet and the isosteviol (ISV) group received standard chow supplemented with 20 mg isosteviol/kg body weight/day. Data are shown as mean±SEM (n=10 in each group). (unpaired), ** p<0.0001.

The effect of ISV treatment on the fasting plasma HDL-cholesterol level in the KKAy group after 9-weeks interventions can be seen from FIG. 4. The plasma HDL-cholesterol concentration has increased by 71% Data are shown in FIG. 4 as mean±SEM (n=10 in each group). (unpaired), ** p<0.0001. Mean±SEM: C57: 1.987±0.071; KKAy: 1.757±0.105; KKAy+Iso: 2.999±0.091.

Changes in Lipid Levels.

Figure 5:
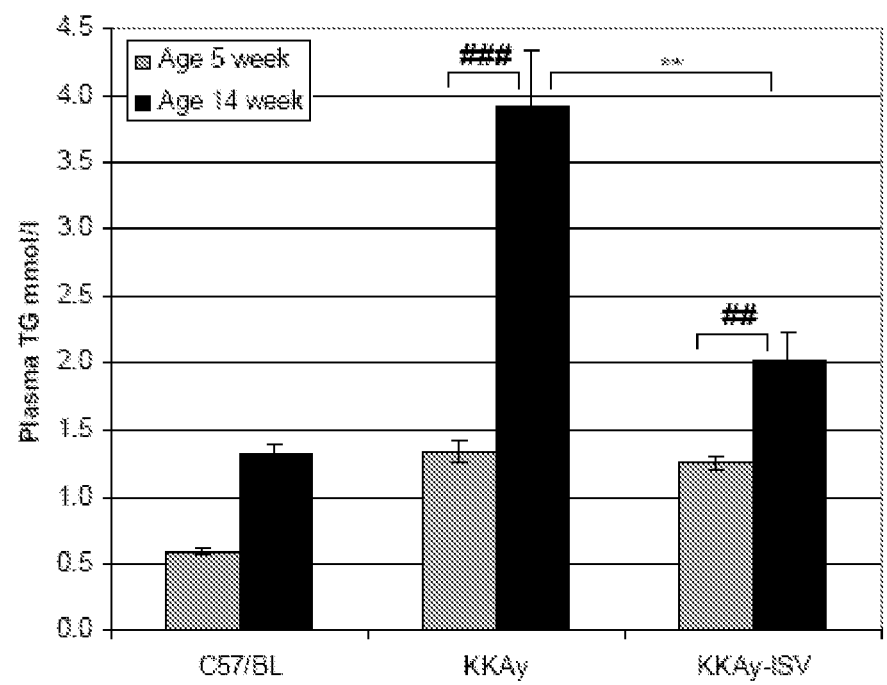
FIG. 5 shows the effect of isosteviol treatment on plasma triglycerides level in KKAy mice before and after 9-weeks interventions. The animals were 5 weeks of age when the treatment began (gray columns), and 14 weeks of age at the end of the treatment period (solid black columns). The C57BL and KKAy control groups received standard chow diet and the isosteviol (ISV) group received standard chow supplemented with 20 mg isosteviol/kg body weight. Data are shown as mean±SEM (n=10 in each group). ** p<0.01 (unpaired), ## p<0.01, ### p<0.001 (paired).

At age 14 weeks the fasting plasma triglyceride (TG) level was increased by 192% for the KKAy control group compared to age 5 week (1.34 vs. 3.92 mmol/l, p<0.001), while the TG level in the ISV group had increased 62% (1.25 vs. 2.02 mmol/l, p=0.003)(FIG. 5). In the ISV group the plasma TG was 48% decreased compared to the KKAy group (3.92 vs. 2.02, p<0.001).

Body Weight

Figure 6:
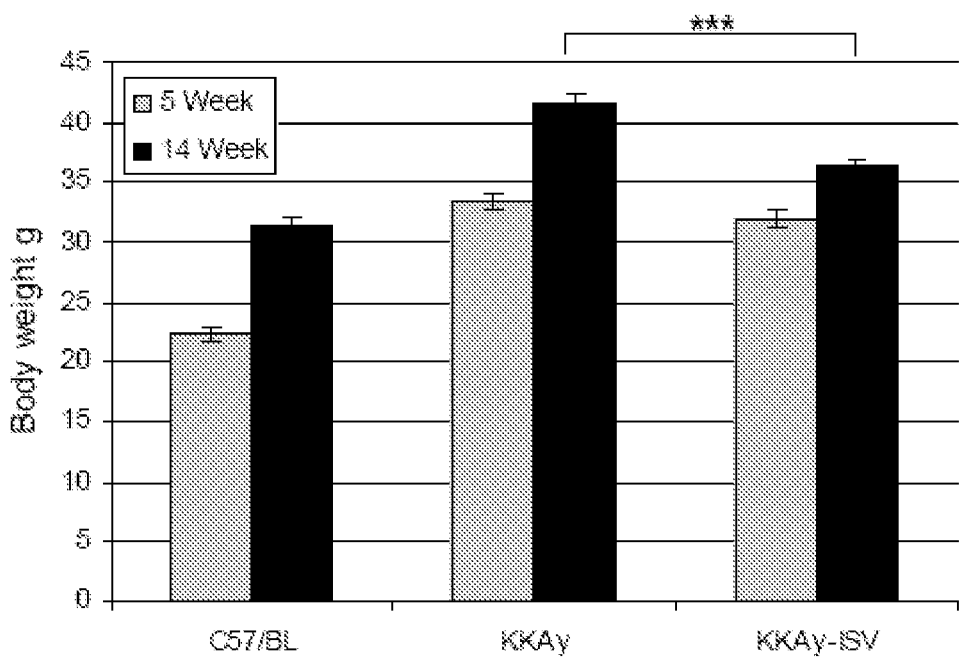
FIG. 6 shows the effects of isosteviol treatment on body weight of KKAy mice. The animals were 5 weeks of age when the treatment began (gray columns), and 14 weeks of age at the end of the treatment period (solid black columns). Data are shown as mean±SEM (n=10 in each group). *** p<0.001 (unpaired).

At the start of the intervention study, no significant difference was observed in body weight between the KKAy control and the ISV groups (FIG. 6). ISV caused a weight reduction after 9 weeks treatment (KKAy control 41.6 g vs. ISV 36.3 g, respectively). The reduction in weight achieved was 13% (p<0.001) for the ISV group at the end of the 9 week treatment period (FIG. 6). The food intake was measured after 5 week treatment and we found no significant difference between the KKAy control and the ISV group (4.95 vs. 4.9 g, p=0.88). As expected we found difference between the KKAy control and the smaller C57BL mice (3.75 vs. 4.95 g, p<0.001).

Example 2

In Vivo Study: the Effects of Isosteviol Treatment on the Plasma HDL-Cholesterol Level and Body Weight in Rats Material and Methods
Animals 44 normal wistar rats at the age of about 6 weeks and a bodyweight of about 230 g, was randomised into 4 groups, with 11 in each group. Group 1 and 2 were fed with standard chow diet±Isosteviol (0.03 g/kg/day). Group 3 and 4 were diet induced to be hyperlipidemic by feeding with a high cholesterol containing diet (1.63% g cholesterol, 0.41% g Cholic acid, 16.3% g sunflower oil)±Isosteviol (0.03 g/kg/day). In the experiment was used Isosteviol with a purity of 99.4%. The treatment period was 20 weeks.

Sample Analysis

Blood samples were analyzed for hormones and lipids at the start and end of the study. The blood samples were taken from the tail or eye into glasses containing heparine/aprotinin. The samples were centrifuged and the plasma was frozen. The following were analyzed: total fasting plasma triglyceride level, total plasma cholesterol level, and plasma HDL-cholesterol level. Liver samples were analysed for mRNA expression of genes like SREBP-1, which have relation to the fat metabolism. The body weight was measured throughout the study period together with the food intake.

Assays

The fasting total plasma cholesterol level and the HDL-cholesterol level were measured by an enzymatic colorimetric test, the "cholesterol CHOD-PAP" method (cholesterol oxidase±phenol 4 amino phenazon), based on Trinder, using commercially available test kits (Roche Diagnostics, Basel, Germany), and the Cobas Mira instrument (Roche Diagnostics). The fasting plasma triglyceride level was measured by the enzymatic colorimetric GPO-PAP method (Glycerol phosphate oxidase±phenol 4 amino phenazon), based on Trinder, using commercially available test kits (Roche Diagnostics, Basel, Germany), and the Cobas Mira instrument (Roche Diagnostics).

Statistical Analysis

Data are expressed as means±standard error of the mean (SEM). Statistical significance between two groups was evaluated using a two-tailed t test. A p value of less than 0.05 was considered statistically significant. For statistical analysis were used student t-tests and two way ANOVA-tests.

Design

The drug is evaluated to have a specific positive effect, if the plasma HDL-cholesterol level is increased a few percentage. Analysis of human data have shown that an increase about 1 mg per deciliter (0.03 mmol/l) in the plasma HDL-cholesterol level minimizes the risk for developing cardiovascular diseases by 2-3%.

The setup differs from the setup in Example 1 by the use of non-diabetic rats versus the diabetic hyperlipidemic KKAY mouse model. In the present study the effect on HDL is investigated by comparing rats with a normal cholesterol level with rats having a diet induced elevated plasma cholesterol level.

Results

Figure 7A:
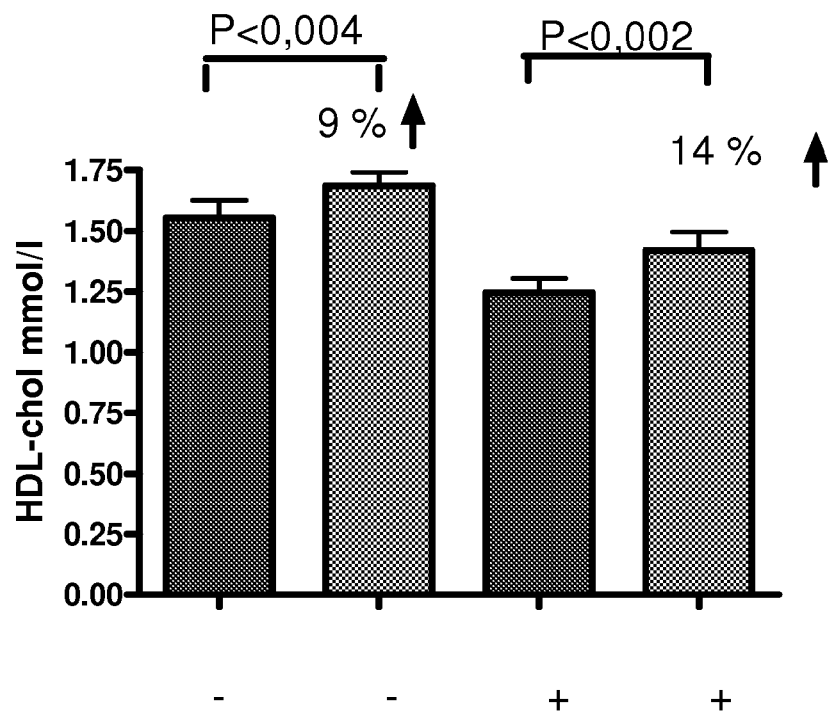
FIG. 7A shows the effect of isosteviol treatment on the plasma HDL level in normal Wistar rats given a normal chow diet. The animals were approximately 6 weeks of age when the treatment began (black columns), and the treatment lasted for 20 weeks (chequered columns). Control, i.e. untreated animals, are given to the left, and isosteviol treated animals are given to the right. Data are shown as mean±SEM (n=11 in each group).
Figure 7B:
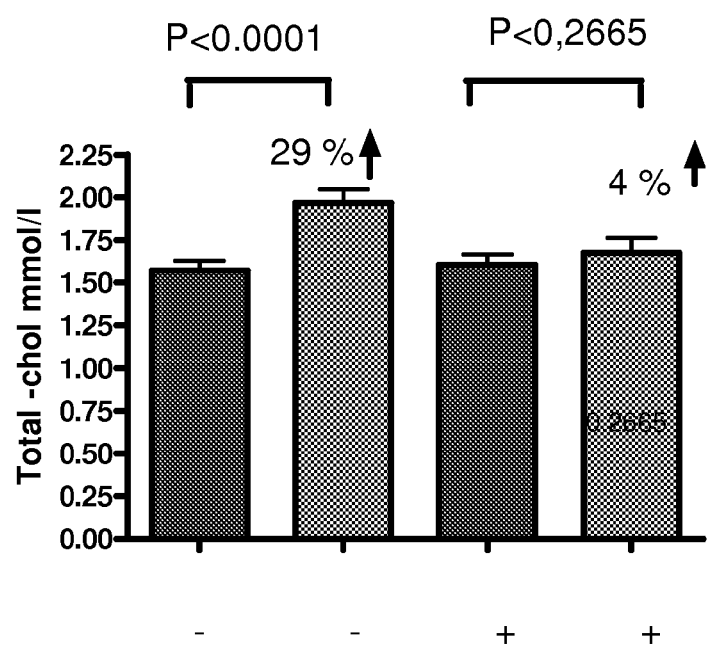
FIG. 7B shows the effect of isosteviol treatment on the total plasma cholesterol level in normal Wistar rats given a normal chow diet. The animals were approximately 6 weeks of age when the treatment began (black columns), and the treatment lasted for 20 weeks (chequered columns). Control, i.e. untreated animals are given to the left, and isosteviol treated animals are given to the right. Data are shown as mean±SEM (n=11 in each group).

Changes in HDL and Fasting Total Plasma Cholesterol Levels—Group 1 and 2, Chow Diet The effect of ISV treatment on the plasma HDL-cholesterol and on the fasting plasma total cholesterol level in group 1 (−isosteviol) and 2 (+isosteviol) after 20 weeks of treatment and chow diet can be seen from FIG. 7A and FIG. 7B, respectively. Group 1 is to the left of the figures, group 2 to the right; black columns represent measurements at start of study and chequered columns represent measurements after 20 weeks. The Results are furthermore shown in Table 1.

The plasma HDL-cholesterol level has increased by 9% for group 1 (−isosteviol) (Δ0.13±0.04 (SEM) mmol/l; p<0.004), and increased by 14% for group 1 (+isosteviol) (Δ−0.17±0.04 (SEM) mmol/l; p<0.002) from start to end of the study, both of which are considered statistically significant increases.

The fasting total plasma cholesterol level has increased by 29% for group 1 (−isosteviol) (Δ0.39±0.06 (SEM) mmol/l; p<0.0001) from start to end of the study, which is considered a statistically significant increase; and increased by 4% for group 2 (+isosteviol) (Δ0.07±0.06 mmol/l; p<0.267) from start to end of the study, which is considered a statistically non-significant increase.

In rodents as e.g. in mice and rats, the major part of total cholesterol is formed by HDL-cholesterol. This is in contrast to human subjects where LDL-cholesterol constitutes the main component of total cholesterol and HDL cholesterol only forms a small part. Elevated total cholesterol in rats in this study may thus reflects an increase in HDL cholesterol and an improved lipid profile, whereas a high total cholesterol in humans normally is caused by elevated LDL cholesterol, i.e. a negative lipid profile. Accordingly, from the present study groups 1 and 2 it can be seen that isosteviol increases the plasma HDL-cholesterol level when the rats are on a normal diet, and furthermore increases the HDL-cholesterol level more than the total cholesterol level.

Figure 8A:
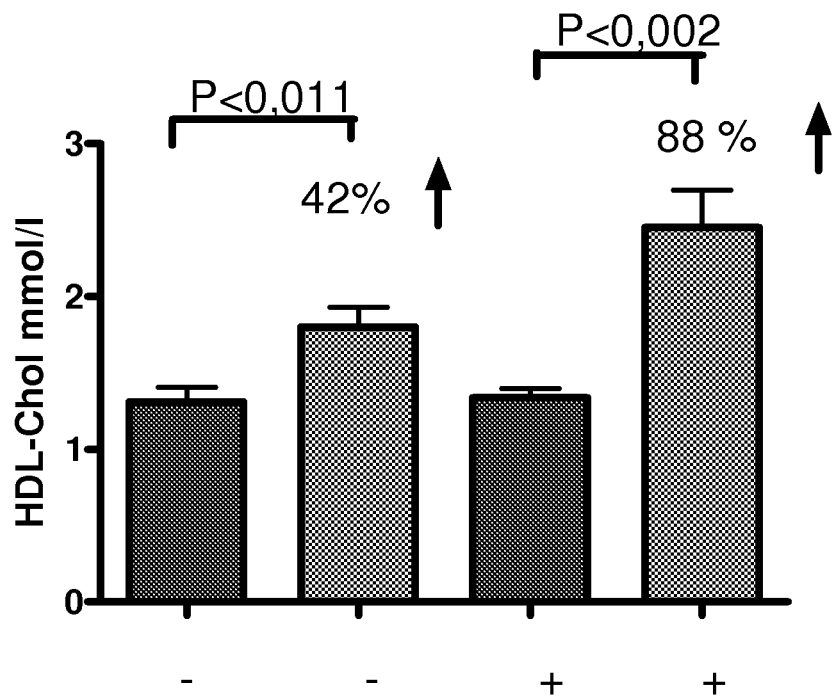
FIG. 8A shows the effect of isosteviol treatment on the plasma HDL level in normal Wistar rats given a high fat diet. The animals were approximately 6 weeks of age when the treatment began (black columns), and the treatment lasted for 20 weeks (chequered columns). Control, i.e. untreated animals are given to the left, and isosteviol treated animals are given to the right. Data are shown as mean±SEM (n=11 in each group).
Figure 8B:
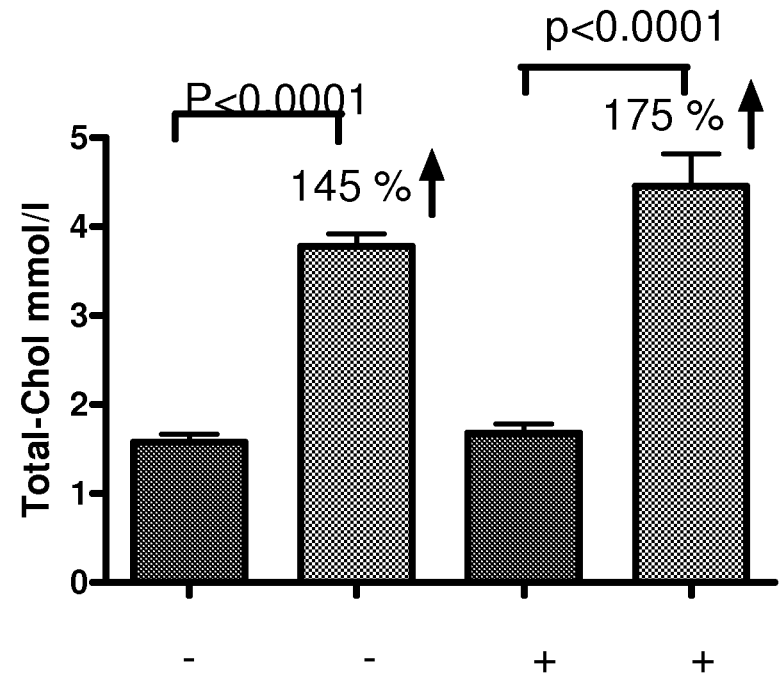
FIG. 8B shows the effect of isosteviol treatment on the total plasma cholesterol level in normal Wistar rats given a high fat diet. The animals were approximately 6 weeks of age when the treatment began (black columns), and the treatment lasted for 20 weeks (chequered columns). Control, i.e. untreated animals are given to the left, and isosteviol treated animals are given to the right. Data are shown as mean±SEM (n=11 in each group).

Changes in HDL and Fasting Total Plasma Cholesterol Levels—Group 3 and 4, High Fat Diet The effect of ISV treatment on the plasma HDL-cholesterol and on the fasting plasma total cholesterol level in group 3 (−isosteviol) and 4 (+isosteviol) after 20 weeks of treatment and high fat diet can be seen from FIG. 8A and FIG. 8B, respectively. Group 3 is to the left of the figures, group 4 to the right; black columns represent measurements at start of study, and chequered columns represent measurements after 20 weeks.

The plasma HDL-cholesterol level has increased by 42% for group 3 (−isosteviol) (Δ0.49±0.15 (SEM) mmol/l; p<0.011), and increased by 88% for group 4 (+isosteviol) (Δ1.11±0.26 (SEM) mmol/l; p<0.002) from start to end of the study, both of which are considered statistically significant increases.

The fasting total plasma cholesterol level has increased by 145% for group 3 (−isosteviol) (Δ2.2±0.14 (SEM) mmol/l; p<0.0001), and increased by 175% for group 4 (+isosteviol) (Δ2.77±0.38 mmol/l; p<0.0001) from start to end of the study, both of which are considered statistically significant increases.

No deaths were observed for group 2 and 4 being treated with isosteviol, whereas two deaths occurred in group 3 being feed with a high fat diet and no isosteviol. This further supports the protective effect of isosteviol against lipid-profile related diseases such as e.g. atherosclerosis and stroke.

It was expected that the total plasma cholesterol level would increase in group 3 and 4 due to the high content of fat and cholesterol in the diet. The extra increase in the total plasma cholesterol (175% vs. 145% for control) for the group being treated with isosteviol is reflected in the high increase of 88% in the plasma HDL-cholesterol level, compared to 42% for the control group. The extra increase in the total plasma cholesterol may also be reflected in the distribution between HDL- and e.g. LDL-cholesterol for rodents, as described above.

Body Weight

Figure 9:
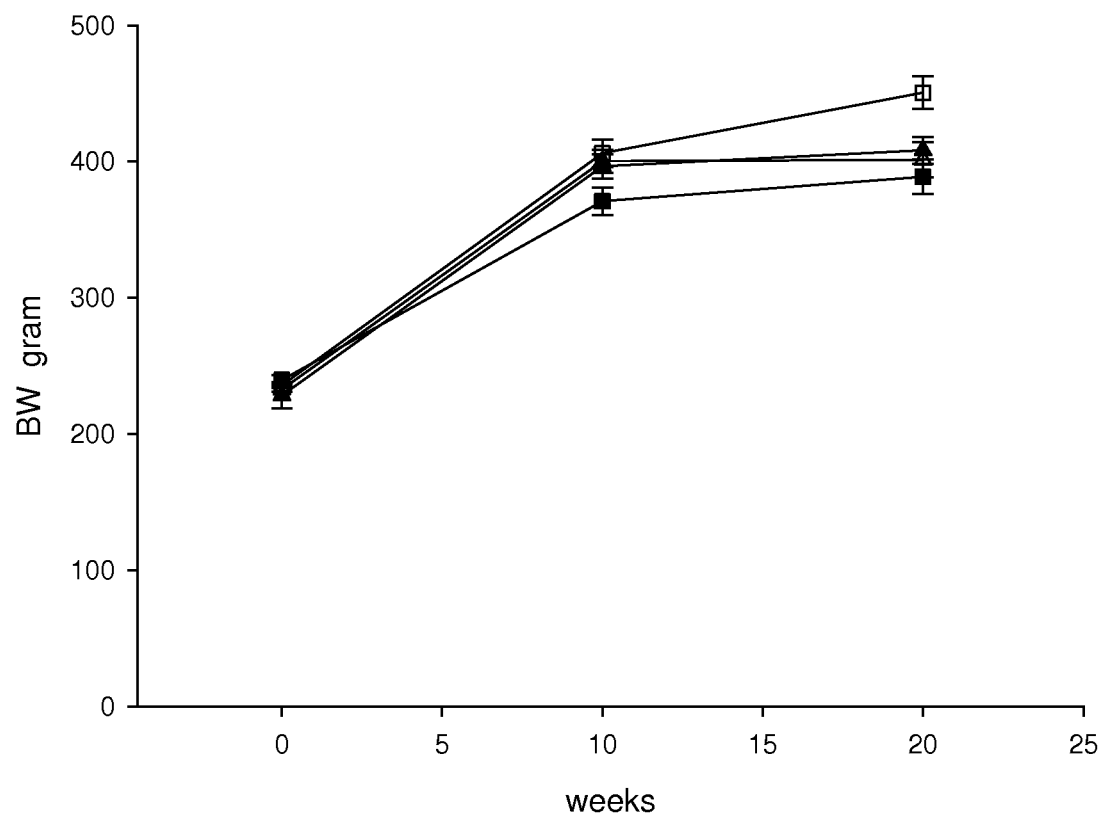
FIG. 9 shows the effect of isosteviol treatment on the body weight of normal Wistar rats given a high fat diet. The animals were approximately 6 weeks of age when the treatment began, i.e. 0 weeks, and the treatment lasted for 20 weeks. The control groups, i.e. untreated animals are marked by white symbols, and isosteviol treated animals are marked by black symbols. Squares represent normal chow diet, and triangles represent high fat diet. Data are shown as mean±SEM (n=11 in each group).

The development in body weight during the 20 weeks period can be seen from FIG. 9, where white symbols represent the control groups 1 and 3 (−isosteviol) and black symbols represent the groups 2 and 4 being treated with isosteviol (+isosteviol). Squares indicate chow diet and triangles indicate high fat diet.

The body weight was reduced by 16% during the 20 weeks for group 2, chow diet+isosteviol compared to group 1, chow diet control. A significant reduction in weigh of 16% was observed for group 2 compared to group 1 after the 20 weeks of treatment (mean±SEM) (450±12 g vs 388±13 g; p<0.002), and was already present from 10 weeks of treatment (406±10 g vs 371±10 g; p<0.023).

Changes in Lipid Levels.

Figure 10:
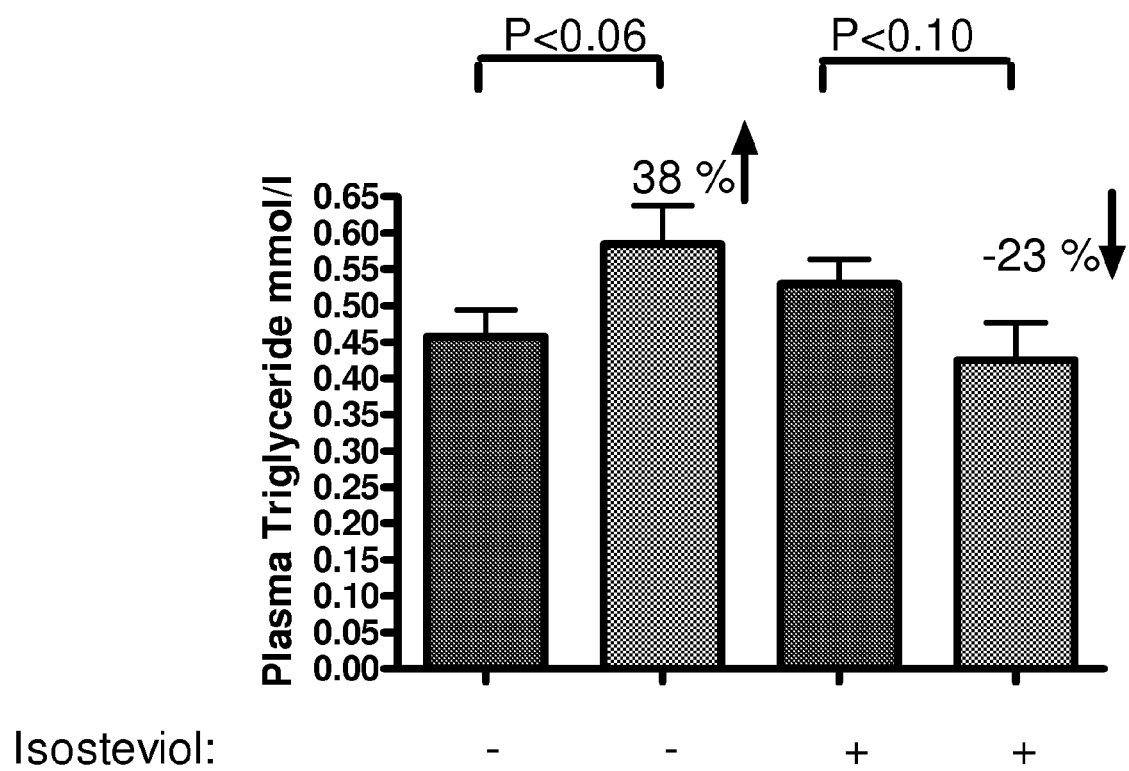
FIG. 10 shows the effect of isosteviol treatment on the fasting plasma triglyceride level of normal Wistar rats given a normal chow diet. The animals were approximately 6 weeks of age when the treatment began (black columns), i.e. 0 weeks, and the treatment lasted for 20 weeks (chequered columns). Control, i.e. animals before and after 20 weeks on chow diet without isosteviol are given to the left, and isosteviol treated animals before and after 20 weeks on chow diet are given to the right. Data are shown as mean±SEM (n=11 in each group).

The effect of ISV treatment on the fasting plasma triglyceride level in group 1 (−isosteviol) and 2 (+isosteviol) after 20 weeks of treatment and normal chow diet can be seen from FIG. 10. Group 1 is to the left of the figure, group 2 to the right; black columns represent measurements at start of study, and chequered columns represent measurements after 20 weeks.

The fasting plasma triglyceride level has for the non treated group 1 (−isosteviol) increased by 38% (P<0.10) (corresponding to an increase of 0.13±0.06 mmol/l; p<0.06). In the treated group 2 (+isosteviol) isosteviol caused a decrease in the triglyceride concentration by 23% (p<0.10) (corresponding to a decrease in the triglyceride concentration of −0.16±0.09 mmol/l; p<0.1), which is considered a statistically non-significant increase for the individual animals. When comparing the two groups at the end of the study period it was found, that isosteviol caused a significant reduction in the triglyceride concentration (Δchange: in absolute values: −0.28±0.10 mmol/l; p<0.02 and in %: 61±18%; p<0.004). Data are shown as mean±SEM.

TABLE 1

|  | High fat Start/End −Isosteviol | High fat Start/End +Isosteviol | Chow Start/End −Isosteviol | Chow Start/End +Isosteviol |
| --- | --- | --- | --- | --- |
| Total Cholesterol MM | 1.58 ± 0.09 3.78 ± 0.14 | 1.68 ± 0.1 4.46 ± 0.37 | 1.57 ± 0.06 1.97 ± 0.08 | 1.61 ± 0.06 1.67 ± 0.09 |
| Δ Abs(mM) Δ in % | 2.20 ± 0.14 145% | 2.77 ± 0.38 175% | 0.39 ± 0.06 29% | 0.07 ± 0.06 4% |
| HDL cholesterol MM | 1.31 ± 0.10 1.80 ± 0.13 | 1.34 ± 0.06 2.45 ± 0.25 | 1.55 ± 0.07 1.68 ± 0.06 | 1.25 ± 0.06 1.42 ± 0.08 |
| Δ Abs(mM) Δ in % | 0.49 ± 0.15 42% | 1.11 ± 0.26 88% | 0.13 ± 0.04 9% | 0.17 ± 0.04 14% |

Example 3

Preparation of Steviol

Stevioside (100 g) was dissolved in water and chemically degraded into steviol by treating stevioside with sodium periodate (150 g) and sodium hydroxide (750 g) according to the method described by Ogawa, T. et al., *Total Synthesis of Stevioside*, Tetrahedron, (1980), 36(18), 2641-2648. The residue obtained after extractive work-up (dichloromethane) of the reaction mixture was repeatedly chromatographed on a 5.5×80 cm column containing silica gel (particle size 63-200 μm; Merck, Darmstadt, Germany) eluting with $CH_2CN$—$CH_3OH$ (49:1, v/v). Fractions containing pure steviol, as shown by thin-layer chromatography (TLC) [silica gel 60 $F^{254}$, layer thickness 0.25 mm, Merck, Darmstadt, Germany; solvent:$CH_3CN$—$H_2O$ (9:1, v/v)] by comparison with an authentic standard (purchased from Extrasynthese, Genay, France), were combined and the solvent removed in vacuo (30° C.). Crystallization from methanol gave pure steviol (1.68 g). The purified steviol was identified by $^{13}C$-NMR and the spectral data were found to be in accordance with literature values (Kohda, H. et al, *New diterpene glucosides from Stevie rebaudiana*, Phytochemistry, 1976; 15:981-983).

$^{13}C$-NMR (75 MHz, $CDCl_3$, TMS in std.): δ 15.5 (C20), 19.0 (C-2), 20.5 (C-11), 21.8 (C-6), 28.8 (C-18), 37.7 (C-3), 39.3 (C-10), 39.5 (C-12), 40.5 (C-1), 41.2 (C-7), 41.7 (C-8), 43.6 (C-4), 47.0 (C-14), 47.4 (C-15), 53.8 (C-9), 56.9 (C-5), 80.3 (C-13), 103.0 (C-17), 155.8 (C-16), 183.1 (C-19).

Example 4

Preparation of Isosteviol

Stevioside (100 g) was dissolved in water and chemically degraded into Isosteviol by treating stevioside with 2N HCl (2000 ml). The reaction mixture was refluxed for 2 h and filtered to give a solid. The residue obtained after extractive work-up (dichloromethane) of the reaction mixture was repeatedly chromatographed on a 5.5×80 cm column containing silica gel (particle size 63-200 μm; Merck, Darmstadt, Germany) eluting with $CH_2CN$—$CH_3OH$ (49:1, v/v). Fractions containing pure Isosteviol, as shown by thin-layer chromatography (TLC) [silica gel 60 $F^{254}$, layer thickness 0.25 mm, Merck, Darmstadt, Germany; solvent:$CH_3CN$—$H_2O$ (9:1, v/v)] by comparison with an authentic standard (purchased from Extrasynthese, Genay, France), were combined and the solvent removed in vacuo (30° C.).

$^{13}C$-NMR (75 MHz, $CDCl_3$, TMS int. std.): δ 13.3 (C20), 18.8 (C-2), 20.3 (C-11), 21.6 (C-6), 28.9 (C-18), 37.3 (C-3), 37.6 (C-10), 38.1 (C-12), 39.6 (C-1), 41.4 (C-7), 41.7 (C-8), 43.6 (C-4), 48.4 (C-14), 48.7 (C-15), 54.2 (C-9), 56.9 (C-5), 77.4 (C-13), 184.0 (C-17), 184.0 (C-16), 222.8 (C-19).

References

Anthony G. Avent et al., *hydrolysis of the diterpenoid glycoside, stevioside*, Phytochemistry, 1990, vol. 29, No. 8, pp. 2712-2715.

Barter, P. et al., *HDL Cholesterol, Very low levels of LDL Cholesterol, and Cardiovascular events*"; N. Engl. J. Med., 2007, 357, (13), 1301-10.

Barter P. J., et al., ILLUMINATE Investigators, *Effects of torcetrapib in patients at high risk for coronary events*, N Engl J. Med., 2007, 357(21), 2109-22.

Feng-Lin Hsu et al., in *Microbial transformations of isosteviol*, J. Nat. Prod. (2002), 65, 273-277.

Gordon et al. *High-density lipoprotein and cardiovascular disease. Four prospective American studies.* Circulation, 1989; 79:8-15.

Heding L. G., *Determination of total serum insulin (IRI) in insulin-treated diabetic patients*, Diabetologia, 1972; 8:260-266.

Kohda, H. et al, *New diterpene glucosides from Stevia rebaudiana*, Phytochemistry, 1976; 15:981-983.

Mann, J. I. et al., *Diabetes and Nutrition Study Group (DNSG) of the European Association. Evidence-based nutritional approaches to the treatment and prevention of diabetes mellitus*, Nutr Metab Cardiovasc Dis., 2004, 14(6):373-94.

Mosca, L. et al. and American Heart Association, *Evidence-based guidelines for cardiovascular disease prevention in women*, Circulation; 109 (2004) (5), 672-693.

Nordentoft, I. et al., *Isosteviol increases insulin sensitivity and changes gene expression of key insulin regulatory genes and transcription factors in islets of the diabetic KKAy mouse*, Diabetes Obes Metab., 2008, 10(10):939-49.

Ogawa, T. et al., *Total Synthesis of Stevioside*, Tetrahedron, (1980), 36(18), 2641-2648.

*Prevention of cardiovascular diseases in clinical practice.* Guidelines of the third joint task force of European and other societies on cardiovascular disease prevention in clinical practice. European Heart Journal 2003; 24:1601-1610).

Rader, D. J.; *Illuminating HDL—Is it still a viable therapeutic target?*; N. Engl. J. Med.; 2007; 357; 21, p. 2180-2183.

The invention claimed is:

1. A method for elevating the plasma HDL-cholesterol level in a human subject in need thereof, the method comprising administering to said human subject a daily dose of at least 100 mg of a plasma HDL-cholesterol level elevating amount of a compound selected from the group consisting of steviol and isosteviol, or a pharmaceutically acceptable salt or solvate thereof.

2. The method according to claim 1, wherein the plasma HDL-cholesterol level is elevated by at least 2 mg/dl (0.06 mmol/l).

3. The method according to claim 1, wherein the plasma HDL-cholesterol level is elevated to a level of at least 35 mg/dl (1.0 mmol/l) for men and a level of at least 42 mg/dl (1.20 mmol/l) for women.

4. The method according to claim 1, wherein the daily dosage is in a range of from about 100 mg to about 1500 mg.

5. The method according to claim 4, wherein the daily dosage is in a range selected from the group consisting of from about 100 mg to about 1000 mg and from about 500 mg to about 1000 mg.

6. The method according to claim 1, wherein the method is for at the same time elevating the plasma HDL-cholesterol level and reducing the body weight of a subject.

7. The method according to claim 6, wherein the body weight is reduced by an amount selected from the group consisting of at least about 5%, at least about 8%, at least about 10%, at least about 12%, at least about 15%, at least about 18%, at least about 20%, at least about 22%, and at least about 25%.

8. The method according to claim 1, wherein the compound is isosteviol, or a pharmaceutically acceptable salt or solvate thereof.

9. The method according to claim 1, wherein the compound is a mixture of steviol and isosteviol, or pharmaceutically acceptable salts or solvates thereof.

10. The method according to claim 1, wherein the plasma triglyceride level is lowered.

11. The method according to claim 1, wherein the fasting plasma triglyceride level is lowered by about 5% to about 50%.

12. The method according to claim 1, wherein the compound is given in a daily dosage in a range selected from the group consisting of from about 100 mg to about 500 mg, about 100 mg to about 400 mg, about 100 mg to about 300 mg, about 100 mg to about 200 mg, about 200 mg to about 500 mg, about 200 mg to about 400 mg, and about 200 mg to about 300 mg.

13. The method according to claim 1, wherein the compound is given in a daily dosage in a range selected from the group consisting of about 500 mg to about 1000 mg, about 500 mg to about 900 mg, about 500 mg to about 800 mg, about 500 mg to about 700 mg, about 500 mg to about 600 mg, about 600 mg to about 1000 mg, about 700 mg to about 1000 mg, about 800 mg to about 1000 mg, about 900 mg to about 1000 mg, and about 600 mg to about 900 mg.

14. The method according to claim 1, wherein the compound is given in a daily dosage in a range selected from the group consisting of about 1000 mg to about 1500 mg, about 1000 mg to about 1400 mg, about 1000 mg to about 1300 mg, about 1000 mg to about 1200 mg, about 1000 mg to about 1100 mg, about 1100 mg to about 1500 mg, about 1200 mg to about 1500 mg, about 1300 mg to about 1500 mg, about 1400 mg to about 1500 mg, and about 1100 mg to about 1400 mg.

15. The method according to claim 1, wherein the daily dosage is in a range selected from the group consisting of about 0.14 to about 21 mg/kg, about 1.5 to about 14 mg/kg, and about 7 to about 14 mg/kg.

16. The method according to claim 1, wherein the compound is administered in combination with one or more additional active compounds.

17. The method according to claim 1, wherein the compound is formulated in a composition further comprising one or more additional active compounds.

18. The method according to claim 16, wherein the one or more additional active compounds are selected from the group consisting of insulin, sulfonylureas, meglitinides, biguanides, thiazolidinediones, glitazones, α-glucosidase inhibitors, incretin mimetics, GLP-1 analogues, GLP-1 agonists, DPP-4 inhibitors, amylin analogues, PPAR α/γ ligands, sodium-dependent glucose transporter 1 inhibitors, fructose 1,6-bisphosphatase inhibitors, glucagon inhibitors, and 11beta-HSD1 inhibitors.

19. The method according to claim 16, wherein the one or more additional active compounds are selected from the group consisting of thiazides, diuretics, ACE inhibitors, AT2 inhibitors, ARB, $Ca^{2+}$ antagonists, α-blockers, β-blockers, cholesterol absorption inhibitors, hypolipidemic drugs, fibrates, anion exchangers, bile acid sequestrants, fish oils, HMG-CoA reductase inhibitors, and CB1 cannabinoid receptor antagonists.

20. The method according to claim 16, wherein the one or more additional active compounds are selected from the group consisting of insulin, glimepiride, glibenclamide, tolbutamide, gliclazide, glipzid, repaglinide, nateglinide, metformin, pioglitazones, rosiglitazones, acarbose, miglitol, liraglutide, exenatide, sitagliptin, vildagliptin saxagliptin, and alogliptin.

21. The method according to claim 16, wherein the one or more additional active compounds are selected from the group consisting of bendroflumetiazid, indapamid, hydrochlorothiazid, captopril, enalapril, lisinopril, fosinopril, perindopril, quinapril, ramipril, trandolapril, quinapril, fosinopril, candesartancilexetil, irbesartan, losartan, valsartan, telmisartan, eprosartan, olmesartanmedoxomil, nifedipin, amlodipin, nitrendipin, diltiazem, felodipin, verapamil, lacidipin, isradipin, lercanidipin, doxazosin, prazosin, terazosin, phentolamin, hydralazin, acebutolol, atenolol, bisoprolol, carvedilol, esmolol, labetalol, metoprolol, pindolol, propranolo, sotalol, tertatolol, timolol, methyldopa, moxonidin, ezitimibe, gemfibrozil, bezafibrat, fenofibrate, nicotinic acid, acipimox, colestipol, colestyramin, fish oils, atorvastatin, fluvastatin, lovastatin, pravastatin, rosuvastatin, simvastatin, rosuvastatin, pitavastatin, mevastatin, cerivastatin, and rimonabant.

22. The method according to claim 16, wherein one of the one or more additional active compounds is selected from the group consisting of LDL-cholesterol lowering agents, triglyceride lowering agents, cholesterol synthesis inhibitors, cholesterol absorption inhibitors, MTP/Apo B secretion inhibitors, fibrates, niacin, ion-exchange resins, antioxidants, ACAT inhibitors, and bile acid sequestrants.

23. The method according to claim 22, wherein the LDL-cholesterol lowering agent is selected from the group consisting of HMG-CoA reductase inhibitors and MTP/Apo B secretion inhibitors.

24. The method according to claim 16, wherein one of the one or more additional active compounds is selected from the group consisting of atorvastatin, fluvastatin, lovastatin, pravastatin, rosuvastatin, simvastatin, rosuvastatin, pitavastatin, mevastatin, and cerivastatin.

25. The method according to claim 1, wherein the method is for at the same time elevating the plasma HDL-cholesterol level and lowering the LDL-cholesterol level.

26. The method according to claim 25, wherein the LDL-cholesterol level is lowered to less than 3 mmol/l, to less than 2.5 mmol/l, or to less than 1.8 mmol/l.

27. The method according to claim 1, wherein the method is for at the same time elevating the plasma HDL-cholesterol level and lowering the fasting total plasma cholesterol level.

28. The method according to claim 27, wherein the fasting total plasma cholesterol level is lowered to less than 5 mmol/l.

29. The method according to claim 1, wherein the compound is formulated in a composition for oral, peroral, sublingual, parenteral, intramuscular, topical, buccal, nasal, or inhalation administration.

30. The method according to claim 1, wherein the compound is formulated in a composition for oral administration.

31. A method for elevating the plasma HDL-cholesterol level in a human subject by administering to a human subject in need of such treatment a daily dose of at least 100 mg of a plasma HDL-cholesterol level elevating amount of a compound selected from the group consisting of steviol and isosteviol, or a pharmaceutically acceptable salt or solvate thereof, and measuring the level of plasma HDL-cholesterol in the subject after administering the compound to detect elevated plasma HDL-cholesterol level in the subject.

* * * * *